United States Patent
Yamamoto et al.

(10) Patent No.: US 10,208,304 B2
(45) Date of Patent: Feb. 19, 2019

(54) ADENOVIRUS LIBRARY AND METHODS

(75) Inventors: Masato Yamamoto, Golden Valley, MN (US); Yoshiaki Miura, Roseville, MN (US)

(73) Assignee: REGENTS OF THE UNIVERSITY OF MINNESOTA, Minnepolis, MN (US)

( * ) Notice: Subject to any disclaimer, the term of this patent is extended or adjusted under 35 U.S.C. 154(b) by 348 days.

(21) Appl. No.: 13/447,847

(22) Filed: Apr. 16, 2012

(65) Prior Publication Data

US 2012/0264192 A1 Oct. 18, 2012

Related U.S. Application Data

(60) Provisional application No. 61/475,402, filed on Apr. 14, 2011.

(51) Int. Cl.
C12N 15/10 (2006.01)

(52) U.S. Cl.
CPC ..... *C12N 15/1034* (2013.01); *C12N 15/1037* (2013.01); *C12N 2710/10043* (2013.01); *C12N 2710/10071* (2013.01); *C12N 2800/30* (2013.01)

(58) Field of Classification Search
CPC ............ C12N 15/1034; C12N 15/1058; C12N 15/1086
See application file for complete search history.

(56) References Cited

U.S. PATENT DOCUMENTS

| 6,297,004 | B1 * | 10/2001 | Russell ................. | A61K 48/00 435/235.1 |
| 2009/0074658 | A1 * | 3/2009 | Lupold ............... | C07K 14/005 424/1.11 |
| 2009/0098599 | A1 * | 4/2009 | Von Seggern ....... | C07K 14/005 435/69.1 |

OTHER PUBLICATIONS

Hatanaka, Kazuteru et al, Jul. 2003 Molecular Therapy 8: 158-166.*
Krasnykh, V et al, 1996 Journal of Virology 70: 6839-6846.*
Neylon, C. 2004 Nucleic Acids Research 32: 1448-1459.*
Bewley, Maria C. et al 1999 Science 286: 1579-1583.*
Miura, Yoshiaki et al May 2009 Molecular Therapy vol. 17, Supplement 1: S321.*
Miura et al. (Gene Therapy (2007) 14, 1448-1460).*
Von Seggern et al. (Journal of virology 74.1 (2000): 354-362.).*
Takayama et al. A mosaic adenovirus possessing serotype Ad5 and serotype Ad3 knobs exhibits expanded tropism. Virology, vol. 309, pp. 282-293, 2003.*
Graham et al. Methods for construction of adenovirus vectors. Molecular Biotechnology, vol. 3, pp. 207-220, 1995.*
Wirth et al. Road to precision: recombinase-based targeting technologies for genome engineering. Current Opinion in Biotechnology, vol. 18, pp. 411-419, 2007. (Year: 2007).*
Aoki et al., "Efficient generation of recombinant adenoviral vectors by Cre-lox recombination in vitro," *Mol. Med.* 1999; 5(4): 224-231.
Lupold et al., "A novel method for generating and screening peptides and libraries displayed on adenovirus fiber," *Nucleic Acids Res.*, 2007; 35(20): e138.
Miura et al., "Direct selection of targeted adenovirus vectors by random peptide display on the fiber knob," *Gene Ther.*, 2007; 14(20): 1448-1460.
Miura et al., "Infectivity-selective Oncolytic Adenovirus Developed by High-throughput Screening of Adenovirus-formatted Library," *Molecular Therapy*, 2013; 21(1): 139-148.
Palmer et al., "Improved system for helper-dependent adenoviral vector production," *Mol. Ther.*, 2003; 8(5): 846-852.
Tsuruta et al., "A Fiber-Modified Mesothelin Promoter-Based Conditionally Replicating Adenovirus for Treatment of Ovarian Cancer," *Clin. Cancer Res.*, 2008; 14(11): 3582-3588.
Von Seggern et al., "Adenovirus vector pseudotyping in fiber-expressing cell lines: improved transduction of Epstein-Barr virus-transformed B cells," *J Virol.*, 2000; 74(1): 354-362.

* cited by examiner

*Primary Examiner* — Jennifer Dunston
(74) *Attorney, Agent, or Firm* — Mueting, Raasch & Gebhardt, PA

(57) ABSTRACT

Described herein is a method that generally includes infecting a host cell with a rescue adenovirus, wherein the rescue adenovirus genome comprises a loxP site and encodes at least one marker, and wherein the host cell comprises a library of polynucleotides that complement the adenovirus genome marker and encode a detectable polypeptide; incubating the infected host cell under conditions effective to permit recombination between the adenovirus genome and one or more of the library polynucleotides and the production of recombinant adenovirus particles comprising at least on detectable polypeptide; and detecting the at least one detectable polypeptide. Also described are adenovirus libraries constructed using such a method.

9 Claims, 15 Drawing Sheets
Specification includes a Sequence Listing.

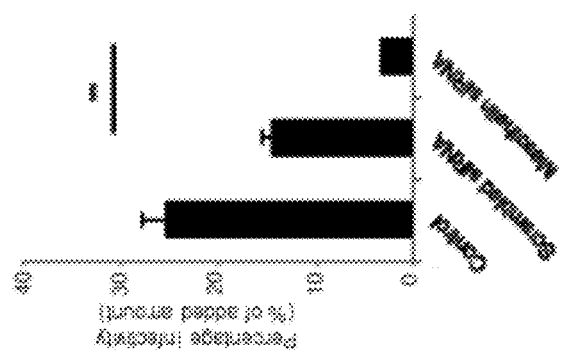
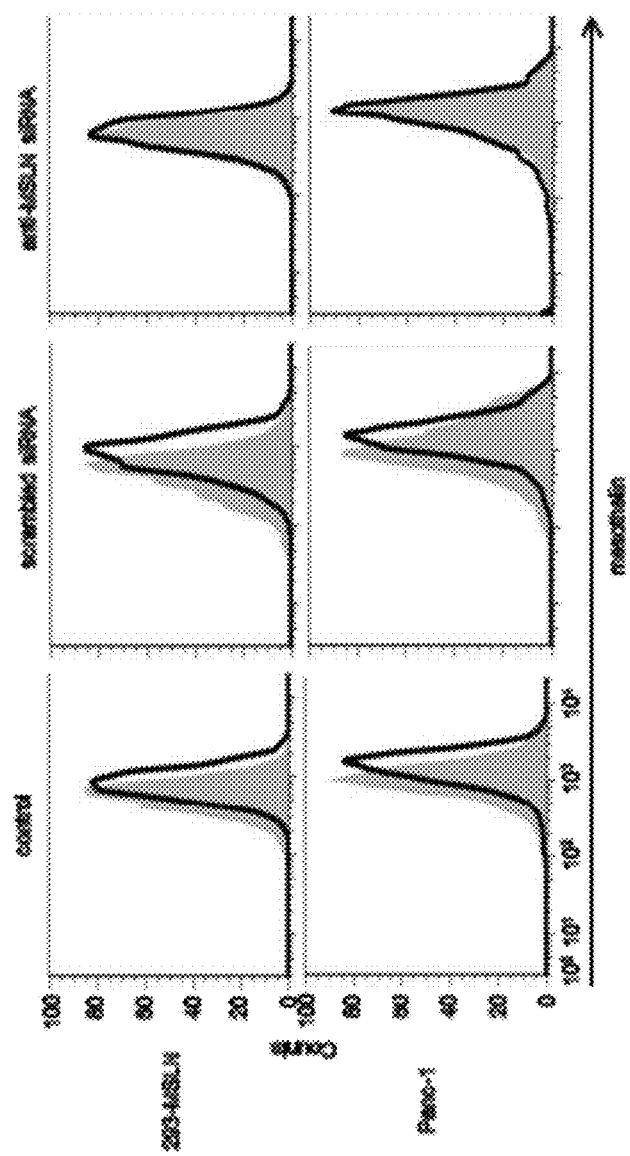
Figure 11a
Figure 11b

SEQUENCE LISTING

<160> NUMBER OF SEQ ID NOS: 60

<210> SEQ ID NO 1
<211> LENGTH: 93
<212> TYPE: DNA
<213> ORGANISM: artificial
<220> FEATURE:
<223> OTHER INFORMATION: synthetic degenerate oligonucleotide
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t

<400> SEQUENCE: 1
aacggtacac aggaaacagg agacacaact ttcgaannkn nknnknnknn knnknnkact      60
agtccaagtg catactctat gtcattttca tgg                                  93

<210> SEQ ID NO 2
<211> LENGTH: 24
<212> TYPE: DNA
<213> ORGANISM: artificial
<220> FEATURE:
<223> OTHER INFORMATION: synthetic oligonucleotide primer

<400> SEQUENCE: 2
gaaacaggag acacaacttt cgaa                                            24

<210> SEQ ID NO 3
<211> LENGTH: 24
<212> TYPE: DNA
<213> ORGANISM: artificial
<220> FEATURE:
<223> OTHER INFORMATION: synthetic oligonucleotide primer

<400> SEQUENCE: 3
catagagtat gcacttggac tagt                                            24

<210> SEQ ID NO 4
<211> LENGTH: 99
<212> TYPE: DNA
<213> ORGANISM: artificial
<220> FEATURE:
<223> OTHER INFORMATION: synthetic degenerate oligonucleotide
<220> FEATURE:
<221> NAME/KEY: misc_feature
<222> LOCATION: (40)..(41)
<223> OTHER INFORMATION: n is a, c, g, or t

```
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t

<400> SEQUENCE: 4
aagctaactt tgtggaccac accagctcca tctcctaacn nknnknnknn knnknnknnk    60
gatgctaaac tcactttggt cttaacaaaa tgtggcagt                          99

<210> SEQ ID NO 5
<211> LENGTH: 20
<212> TYPE: DNA
<213> ORGANISM: artificial
<220> FEATURE:
<223> OTHER INFORMATION: synthetic oligonucleotide primer

<400> SEQUENCE: 5
aagctaactt tgtggaccac                                               20

<210> SEQ ID NO 6
<211> LENGTH: 20
<212> TYPE: DNA
<213> ORGANISM: artificial
<220> FEATURE:
<223> OTHER INFORMATION: synthetic oligonucleotide primer

<400> SEQUENCE: 6
actgccacat tttgttaaga                                               20

<210> SEQ ID NO 7
<211> LENGTH: 24
<212> TYPE: DNA
<213> ORGANISM: artificial
<220> FEATURE:
<223> OTHER INFORMATION: synthetic oligonucleotide primer

<400> SEQUENCE: 7
aattgctagc cctgcaaaca tcag                                          24

<210> SEQ ID NO 8
<211> LENGTH: 21
<212> TYPE: DNA
<213> ORGANISM: artificial
<220> FEATURE:
<223> OTHER INFORMATION: synthetic oligonucleotide primer

<400> SEQUENCE: 8
ggtccacaaa gttagcttat c                                             21
```

<210> SEQ ID NO 9
<211> LENGTH: 21
<212> TYPE: DNA
<213> ORGANISM: artificial
<220> FEATURE:
<223> OTHER INFORMATION: synthetic oligonucleotide primer

<400> SEQUENCE: 9
ttaacaaaat gtggcagtca a                                              21

<210> SEQ ID NO 10
<211> LENGTH: 28
<212> TYPE: DNA
<213> ORGANISM: artificial
<220> FEATURE:
<223> OTHER INFORMATION: synthetic oligonucleotide primer

<400> SEQUENCE: 10
aattcaattg aaaaataaac acgttgaa                                       28

<210> SEQ ID NO 11
<211> LENGTH: 21
<212> TYPE: DNA
<213> ORGANISM: artificial
<220> FEATURE:
<223> OTHER INFORMATION: nucleotide sequence of AB-loop fiber-modified
      adenovirus clone

<400> SEQUENCE: 11
gttactatta atcggtctgc g                                              21

<210> SEQ ID NO 12
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 12

Val Thr Ile Asn Arg Ser Ala
1               5

<210> SEQ ID NO 13
<211> LENGTH: 21
<212> TYPE: DNA
<213> ORGANISM: artificial
<220> FEATURE:
<223> OTHER INFORMATION: nucleotide sequence of AB-loop fiber-modified
      adenovirus clone

<400> SEQUENCE: 13
actcatcttt ctatttatgc t                                              21

<210> SEQ ID NO 14
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 14

Thr His Leu Ser Ile Tyr Ala
1               5

```
<210> SEQ ID NO 15
<211> LENGTH: 20
<212> TYPE: DNA
<213> ORGANISM: artificial
<220> FEATURE:
<223> OTHER INFORMATION: synthetic oligonucleotide primer

<400> SEQUENCE: 15
tgaccctgaa gttcatctgc                                              20

<210> SEQ ID NO 16
<211> LENGTH: 20
<212> TYPE: DNA
<213> ORGANISM: artificial
<220> FEATURE:
<223> OTHER INFORMATION: synthetic oligonucleotide primer

<400> SEQUENCE: 16
gaagtcgtgc tgcttcatgt                                              20

<210> SEQ ID NO 17
<211> LENGTH: 24
<212> TYPE: DNA
<213> ORGANISM: artificial
<220> FEATURE:
<223> OTHER INFORMATION: synthetic oligonucleotide probe
<220> FEATURE:
<221> NAME/KEY: misc_feature
<222> LOCATION: (1)..(1)
<223> OTHER INFORMATION: conjugated to a 6-carboxyfluorescein (6FAM)
      fluorophore
<220> FEATURE:
<221> NAME/KEY: misc_feature
<222> LOCATION: (24)..(24)
<223> OTHER INFORMATION: conjugated to a carboxytetramethylrhodamine
      (TAMRA) fluorophore

<400> SEQUENCE: 17
accctcgtga ccaccctgac ctac                                         24

<210> SEQ ID NO 18
<211> LENGTH: 18
<212> TYPE: DNA
<213> ORGANISM: artificial
<220> FEATURE:
<223> OTHER INFORMATION: synthetic oligonucleotide primer

<400> SEQUENCE: 18
ggagtgcgcc gagacaac                                                18

<210> SEQ ID NO 19
<211> LENGTH: 19
<212> TYPE: DNA
<213> ORGANISM: artificial
<220> FEATURE:
<223> OTHER INFORMATION: synthetic oligonucleotide primer

<400> SEQUENCE: 19
actacgtccg gcgttccat                                               19

<210> SEQ ID NO 20
<211> LENGTH: 20
<212> TYPE: DNA
<213> ORGANISM: artificial
<220> FEATURE:
<223> OTHER INFORMATION: synthetic oligonucleotide primer

<400> SEQUENCE: 20
```
aagctaactt tgtggaccac                                              20

<210> SEQ ID NO 21
<211> LENGTH: 20
<212> TYPE: DNA
<213> ORGANISM: artificial
<220> FEATURE:
<223> OTHER INFORMATION: synthetic oligonucleotide primer

<400> SEQUENCE: 21
actgccacat tttgttaaga                                              20

<210> SEQ ID NO 22
<211> LENGTH: 24
<212> TYPE: DNA
<213> ORGANISM: artificial
<220> FEATURE:
<223> OTHER INFORMATION: synthetic oligonucleotide primer

<400> SEQUENCE: 22
gaaacaggag acacaactttt cgaa                                        24

<210> SEQ ID NO 23
<211> LENGTH: 24
<212> TYPE: DNA
<213> ORGANISM: artificial
<220> FEATURE:
<223> OTHER INFORMATION: synthetic oligonucleotide primer

<400> SEQUENCE: 23
actagtccaa gtgcatactc tatg                                         24

<210> SEQ ID NO 24
<211> LENGTH: 16
<212> TYPE: DNA
<213> ORGANISM: artificial
<220> FEATURE:
<223> OTHER INFORMATION: synthetic oligonucleotide primer

<400> SEQUENCE: 24
gtaaaacgac ggccag                                                  16

<210> SEQ ID NO 25
<211> LENGTH: 17
<212> TYPE: DNA
<213> ORGANISM: artificial
<220> FEATURE:
<223> OTHER INFORMATION: synthetic oligonucleotide primer

<400> SEQUENCE: 25
caggaaacag ctatgac                                                 17

<210> SEQ ID NO 26
<211> LENGTH: 4
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 26

Ala Ala Trp Val
1

<210> SEQ ID NO 27
<211> LENGTH: 7

```
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 27

Ala Met Tyr Ser Thr Leu Tyr
1               5

<210> SEQ ID NO 28
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone
<220> FEATURE:
<221> NAME/KEY: misc_feature
<222> LOCATION: (6)..(6)
<223> OTHER INFORMATION: Xaa can be any naturally occurring amino acid

<400> SEQUENCE: 28

Asp Ala Arg Val Asp Xaa Asp
1               5

<210> SEQ ID NO 29
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 29

Phe Leu Ala Phe Cys Phe Ala
1               5

<210> SEQ ID NO 30
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 30

Ile His Ser Ala Leu Arg Ala
1               5

<210> SEQ ID NO 31
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone
<220> FEATURE:
<221> NAME/KEY: misc_feature
<222> LOCATION: (6)..(6)
<223> OTHER INFORMATION: Xaa can be any naturally occurring amino acid

<400> SEQUENCE: 31

Ile Arg Val Trp Lys Xaa Ile
1               5

<210> SEQ ID NO 32
<211> LENGTH: 7
<212> TYPE: PRT
```

-continued

```
<213> ORGANISM: artificial
<220> FEATURE:
<223> OTHER INFORMATION: amino acid sequence of AB-loop fiber-modified
      adenovirus clone

<400> SEQUENCE: 32

Ile Tyr Tyr Thr Ile Ser Thr
1               5

<210> SEQ ID NO 33
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 33

Asn Arg Arg Thr Ile Leu Met
1               5

<210> SEQ ID NO 34
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 34

Pro Gly Ala Gly Trp Arg Pro
1               5

<210> SEQ ID NO 35
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 35

Arg Asn Asn Asp Asp Thr Leu
1               5

<210> SEQ ID NO 36
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 36

Arg Val Ser Arg Asn Arg Leu
1               5

<210> SEQ ID NO 37
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 37

Ser Glu Arg Gly Asp Trp Ala
1               5
```

```
<210> SEQ ID NO 38
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 38

Val Glu Val Gly Gly Gly Trp
1               5

<210> SEQ ID NO 39
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 39

Trp Gly Ala Val Phe Gly Gly
1               5

<210> SEQ ID NO 40
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 40

Trp His His Cys Pro Tyr Ser
1               5

<210> SEQ ID NO 41
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 41

Cys Ser Leu Asn Gly Gly Gly
1               5

<210> SEQ ID NO 42
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 42

Glu Gly Arg Arg Val Gly Gly
1               5

<210> SEQ ID NO 43
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone
```

<400> SEQUENCE: 43

Glu Thr Ser Ser Leu Leu Phe
1               5

<210> SEQ ID NO 44
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 44

Gly Gly Arg Glu Lys Lys Asp
1               5

<210> SEQ ID NO 45
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 45

Asn Lys Ala His Phe Gly Asn
1               5

<210> SEQ ID NO 46
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 46

Ser Ser Ile Leu Trp Ile Gly
1               5

<210> SEQ ID NO 47
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 47

Thr Gly Ala Cys Ser Trp Ser
1               5

<210> SEQ ID NO 48
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 48

Val Gly Ala Trp Thr Gly Arg
1               5

<210> SEQ ID NO 49
<211> LENGTH: 7

```
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 49

Val Tyr Pro Thr His Gly Lys
1               5

<210> SEQ ID NO 50
<211> LENGTH: 7
<212> TYPE: PRT
<213> ORGANISM: artificial
<220> FEATURE:
<223> OTHER INFORMATION: amino acid sequence of AB-loop fiber-modified
      adenovirus clone

<400> SEQUENCE: 50

Val Thr Ile Asp Arg Ser Ala
1               5

<210> SEQ ID NO 51
<211> LENGTH: 18
<212> TYPE: DNA
<213> ORGANISM: artificial
<220> FEATURE:
<223> OTHER INFORMATION: nucleotide sequence of wild type HI-loop

<400> SEQUENCE: 51
gacacaactc caagtgca                                                   18

<210> SEQ ID NO 52
<211> LENGTH: 6
<212> TYPE: PRT
<213> ORGANISM: artificial
<220> FEATURE:
<223> OTHER INFORMATION: amino acid sequence of wild type HI-loop

<400> SEQUENCE: 52

Asp Thr Thr Pro Ser Ala
1               5

<210> SEQ ID NO 53
<211> LENGTH: 31
<212> TYPE: DNA
<213> ORGANISM: artificial
<220> FEATURE:
<223> OTHER INFORMATION: nucleotide sequence from background shuttle
      plasmid of HI-loop fiber-modified library

<400> SEQUENCE: 53
gacacaactt tcgaaaacta gtccaagtgc a                                    31

<210> SEQ ID NO 54
<211> LENGTH: 10
<212> TYPE: PRT
<213> ORGANISM: artificial
<220> FEATURE:
<223> OTHER INFORMATION: amino acid sequence from background shuttle
      plasmid of HI-loop fiber-modified library
<220> FEATURE:
<221> NAME/KEY: misc_feature
<222> LOCATION: (7)..(7)
<223> OTHER INFORMATION: Xaa can be any naturally occurring amino acid

<400> SEQUENCE: 54

Asp Thr Thr Phe Glu Asn Xaa Ser Lys Cys
```

<210> SEQ ID NO 55
<211> LENGTH: 54
<212> TYPE: DNA
<213> ORGANISM: artificial
<220> FEATURE:
<223> OTHER INFORMATION: nucleotide sequence from HI-loop random
      mutation fiber-modified library
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t

<400> SEQUENCE: 55
gacacaactt tcgaannknn knnknnknnk nnknnknnka ctagtccaag tgca         54

<210> SEQ ID NO 56
<211> LENGTH: 18
<212> TYPE: PRT
<213> ORGANISM: artificial
<220> FEATURE:
<223> OTHER INFORMATION: amino acid sequence from HI-loop random
      mutation fiber-modified library
<220> FEATURE:
<221> NAME/KEY: misc_feature
<222> LOCATION: (7)..(13)
<223> OTHER INFORMATION: Xaa can be any naturally occurring amino acid

<400> SEQUENCE: 56

Asp Thr Thr Phe Glu Asn Xaa Xaa Xaa Xaa Xaa Xaa Xaa Thr Ser Pro
1               5                   10                  15

Ser Ala

<210> SEQ ID NO 57
<211> LENGTH: 42
<212> TYPE: DNA
<213> ORGANISM: artificial
<220> FEATURE:
<223> OTHER INFORMATION: nucleotide sequence of wild type AB-loop

<400> SEQUENCE: 57
acaccagctc catctcctaa ctgtagacta aatgcagagg aa                     42

```
<210> SEQ ID NO 58
<211> LENGTH: 14
<212> TYPE: PRT
<213> ORGANISM: artificial
<220> FEATURE:
<223> OTHER INFORMATION: amino acid sequence of wild type AB-loop

<400> SEQUENCE: 58

Thr Pro Ala Pro Ser Pro Asn Cys Arg Leu Asn Ala Glu Lys
1               5                   10

<210> SEQ ID NO 59
<211> LENGTH: 42
<212> TYPE: DNA
<213> ORGANISM: artificial
<220> FEATURE:
<223> OTHER INFORMATION: nucleotide sequence from AB-loop random
      mutation fiber-modified library
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t

<400> SEQUENCE: 59
acaccagctc catctcctaa cnnknnknnk nnknnknnkn nk                          42

<210> SEQ ID NO 60
<211> LENGTH: 14
<212> TYPE: PRT
<213> ORGANISM: artificial
<220> FEATURE:
<223> OTHER INFORMATION: amino acid sequence from AB-loop random
      mutation fiber-modified library
<220> FEATURE:
<221> NAME/KEY: misc_feature
<222> LOCATION: (8)..(14)
<223> OTHER INFORMATION: Xaa can be any naturally occurring amino acid

<400> SEQUENCE: 60

Thr Pro Ala Pro Ser Pro Asn Xaa Xaa Xaa Xaa Xaa Xaa Xaa
1               5                   10
```

ADENOVIRUS LIBRARY AND METHODS

CROSS-REFERENCE TO RELATED APPLICATION

This application claims priority to U.S. Provisional Patent Application Ser. No. 61/475,402, filed Apr. 14, 2011, which is incorporated by reference in its entirety.

GOVERNMENT FUNDING

This invention was made with government support under CA094084 and CA196215 awarded by the National Institutes of Health. The government has certain rights in the invention.

BACKGROUND

SEQUENCE LISTING

This application contains a Sequence Listing electronically submitted via EFS-Web to the United States Patent and Trademark Office as an ASCII text file entitled "Sequence-Listing11003460101$_{13}$ ST25.txt" having a size of 16 kilobytes and created on Apr. 23, 2012. The information contained in the Sequence Listing is incorporated by reference herein.

SUMMARY

Described herein is a method that generally includes infecting a host cell with a rescue adenovirus, wherein the rescue adenovirus genome comprises a loxP site and encodes at least one marker, and wherein the host cell comprises a library of polynucleotides that complement the adenovirus genome marker and encode a detectable polypeptide; incubating the infected host cell under conditions effective to permit recombination between the adenovirus genome and one or more of the library polynucleotides and the production of recombinant adenovirus particles comprising at least one detectable polypeptide; and detecting the at least one detectable polypeptide.

In some cases, the marker can include a fiber polypeptide and the library of polynucleotides can include a plurality of fiber-encoding regions.

In some cases, infecting the host cell can include adding adenovirus to a culture of host cells at a multiplicity of infection of about 1.

In some cases, the method can include collecting crude viral lysate and re-infecting the host cell with adenovirus in the crude viral lysate. In some of these embodiments, the method can include one or more additional rounds of collecting crude viral lysate and re-infecting the host cell with adenovirus in the crude viral lysate.

In some cases, the method can include producing an adenovirus library that comprises an order of diversity of at least $10^{10}$.

In some cases, the method can be completed in no more than about 48 hours.

In another aspect, we describe herein an adenovirus library produced by any of the methods summarized above.

In other aspects, we describe herein particular exemplary applications of the technology platform embodied by the methods. Such exemplary applications include identifying motifs in target cells that identify the cells as targets for adenovirus attachment and infection, identifying adenovirus vector structures useful for systemic targeting, generating adenovirus cDNA libraries for new drug identification, and rapid production adenovirus vectors that are less prone to mutation than conventional adenovirus vectors.

In another aspect, this disclosure describes an adenovirus that includes an AB-loop that includes a targeting peptide. In some embodiments, the targeting peptide selectively binds to a tumor cell. In some embodiments, for example, the targeting peptide selectively binds to mesothelin. In some embodiments, the adenovirus, when administered to a subject, exhibits reduced biodistribution in the liver compared to an adenovirus comprising a wild-type AB-loop. In some embodiments, the adenovirus, when administered to a subject, exhibits increased biodistribution in the tumor compared to an adenovirus comprising a wild-type AB-loop.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 11. The inhibition of mesothelin (MSLN) expression with the anti-MSLN siRNA eliminated AdML-VTIN binding to the target cells. (a) Expression of cell surface MSLN was determined by flow-cytometry after the treatment with the anti-MSLN siRNA. Shaded: without anti-MSLN antibody, Black-line: with anti-MSLN antibody. (b) Suppression of MSLN expression with the anti-MSLN siRNA eliminated AdML-VTIN binding to the Panc-1 cells. Mock transfection controls received only the transfection reagent. After the treatment with the siRNA, the binding assay was performed. (**: P<0.01).

DETAILED DESCRIPTION OF ILLUSTRATIVE EMBODIMENTS

Figure 1:
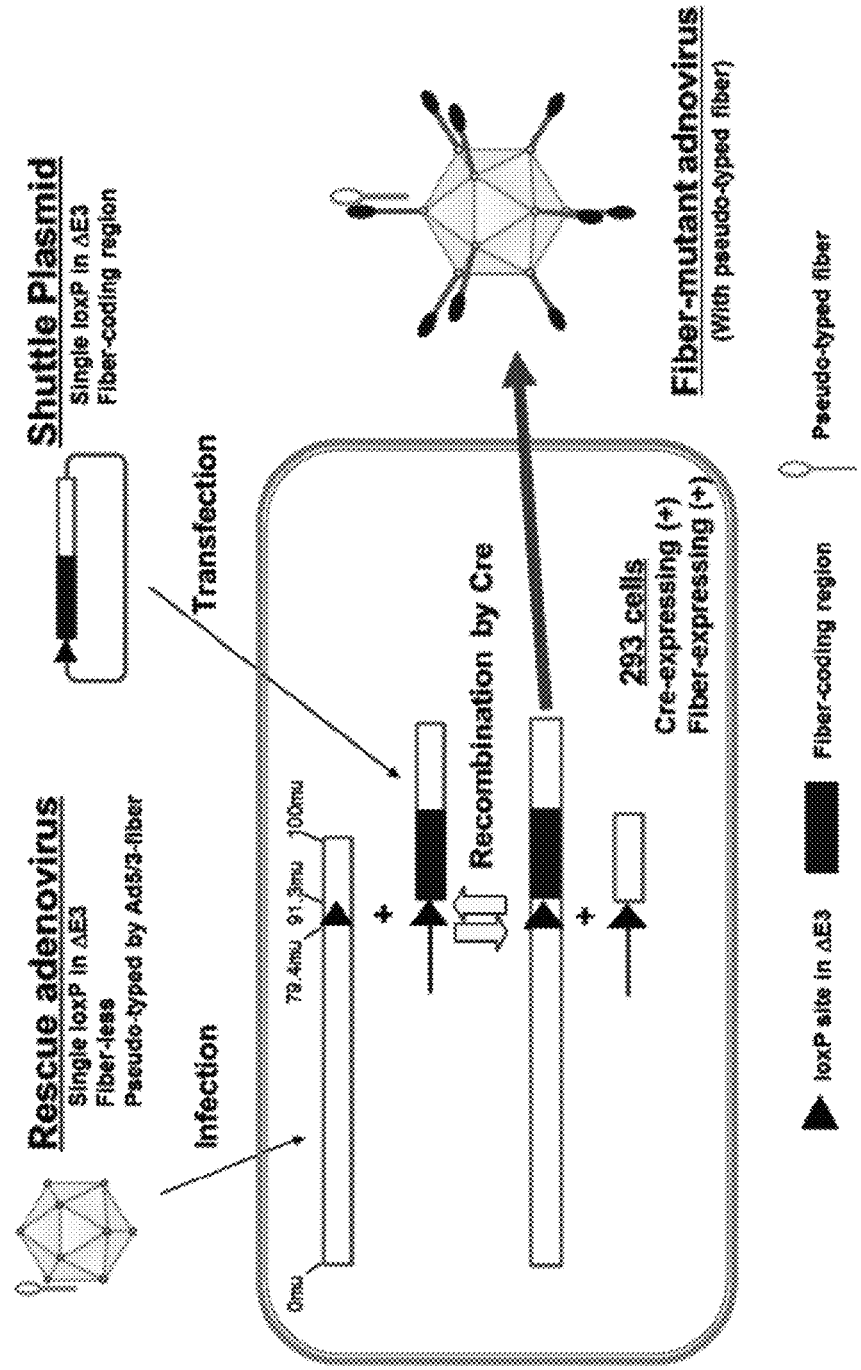
FIG. 1. Basic Strategy for Constructing Fiber-modified Adenovirus Vector. Construction of fiber-modified adenovirus vector. The vector was produced by a Cre-lox recombination system in producer cells between a fiber-modified shuttle plasmid and adenoviral DNA from the rescue virus. The resultant virus was pseudo-typed and replicated in producer cells using fiber-complementing system and could be directly applied following screening steps.

This disclosure describes adenovirus libraries and a method for producing such adenovirus libraries. The methods can exploit recombination between a rescue adenovirus and one of a plurality of shuttle polynucleotides in the host cell. The methods also can involve infecting host cells with adenovirus at a relatively low multiplicity of infection and subsequently collecting crude viral lysate and re-infecting the host cells with adenovirus in the crude viral lysate.

Adenoviruses (Ad) can have high in vitro and in vivo transduction efficiency compared to other viral and non-viral gene transfer methods. Thus, it may be attractive to consider using an adenovirus in the construction of genetic libraries. However, such developments have been hampered by extremely low conversion from virus-coding plasmids to viruses. For example, in a conventional adenovirus vector generation method, 1 μg of plasmid ($3\times10^{10}$ copy) generates only 1-2 plaques of virus, resulting in a viral library yield of only $1/10^{10}$ of the diversity of the plasmid before transfection.

The methods described herein can significantly improve plasmid-to-virus conversion. Thus, such a system can allow library work for finding vector targeting motifs for specific diseases such as, for example, cancers. For example, we describe construction of a transductionally-targeted Infectivity-Selective Oncolytic Adenovirus (ISOAd) for selective cell entry into, and replication in, target tumor cells.

The system also can produce highly efficient cDNA library-expressing vectors, which can be used in various in vitro and in vivo methods such as, for example, drug screening. In addition, the methods can be an advance over conventional methods for Ad vector generation by enabling much quicker vector production and/or result in fewer mutation-prone vectors. To date, multiple groups have tried to improve the plasmid-to-virus conversion but the largest library size reported is at most on the order of $10^6$, which is minimal for cDNA library work and far less than sufficient for fiber library work for exploration of new targeting motif.

Briefly, our system uses engineered shuttle plasmids in which each shuttle plasmid in a plasmid library includes a library sequence and one loxP site. The system also uses a fiber pseudo-typed, genetically fiberless rescue adenovirus with one loxP site. These two components are introduced into specifically modified CRE recombinase-expressing vector producer cells. When our system was applied to the targeting motif library presented in HI-loop and AB-loop regions of adenovirus fiber respectively, we successfully generated libraries with a $10^{10}$ order of diversity. This can be $10^{10}$ times higher than the diversity that is routinely accomplished using conventional plasmid transfection methods and $10^4$ times higher than the largest library size reported in the field of adenovirus vector.

Our system was applied to the targeting motif library presented in AB-loop region of Ad fiber. This region is known to be responsible for the initial binding to the cellular receptor, coxackie-adenvirus receptor (CAR), and thought to be suitable for binding motif presentation. However, all previous trials have failed, presumably due to structural sensitivity of this region for virus assembly. We have, for the first time, successfully generated an adenovirus library with random targeting motifs in AB-loop, and the library size was confirmed to be in the order of $10^{10}$.

The AB-loop library virus was screened with pancreatic cancer cells and the convergence of the library sequence was observed, indicating successful selection. The isolated clone showed high infectivity and replication in the cells used for the selection process, but its infectivity and replication in another pancreatic cancer cell was negligible. This result indicates that a specific targeting motif was isolated by the screening of the adenovirus library.

Thus, we describe methods that can produce extremely high adenovirus vector production and excellent diversity of the library of targeting motif peptides presented compared to conventional methods. The methods can produce, for example, $10^{10}$ diversity of HI-loop and AB-loop libraries. The methods further permit successful identification of a targeting motif that exhibits specific binding of target cells.

The methods may have many different applications. First, the methods may be used, for example, to identify targeting motifs by screening a targeting motif library that presents various targeting motifs in the format of adenovirus. To date, many targeting motifs have been incorporated to adenoviral vector for disease-specific gene delivery such as, for example, cancer cell selective gene therapy. However, the incorporation of a pre-identified peptide motif into an adenoviral capsid has been mostly unsuccessful, and the few peptide motifs successfully incorporated into an adenovirus capsid have generally been non-specific. Our methods can permit high-throughput screening of a high diversity library presented in the form of an adenovirus. Our technology can enable the identification of such disease-specific and/or tissue-specific targeting motifs. One of the motifs we identified using such high-throughput screening showed selective binding and replication in target cells. This serves as an evidence of feasibility of such strategy for targeted vector development.

Second, methods describe herein can be used to identify vector structures useful for systemic targeting. For example, the methods described herein can lead to gene therapy treatment of cancer by administering a systemic vector carrying a therapeutic polynucleotide. Our strategy allows one to produce a highly diverse library of various portions of the adenovirus capsid including, for example, AB-loop, HI-loop, and hexon hyper-variable region (HVR). In particular, for example, hexon HVR can contribute to liver sequestration of adenovirus after systemic delivery. Thus, screening of a hexon HVR library for adenovirus with an increased circulation half-life after systemic administration can lead to the identification of a vector structure that slows and/or decreases liver sequestration, thereby extending circulation half-life and permitting targeted delivery of the vector to target cells (e.g., tumor cells) after systemic administration.

As noted above, we describe construction of a transductionally-targeted Infectivity-Selective Oncolytic Adenovirus (ISOAd) for selective cell entry into, and replication in, target tumor cells. Transductional targeting of oncolytic viruses requires the targeting moiety to be encoded by the virus genome to maintain the same infectivity profile in progeny viruses produced in the tumor. In many cases, incorporating a targeting motif into the Ad capsid can negatively affect adenovirus assembly and/or the affinity or specificity of the introduced ligand. One promising way to overcome this issue is to identify one or more targeting motifs by performing high throughput screening of a ligand library presented, from the outset of analysis, in the virus capsid.

Third, the methods may be used to generate adenovirus cDNA libraries for new drug identification. Our technique can allow one to generate a high diversity adenovirus library with cDNA as a transgene. Because adenoviruses can exhibit high in vitro and in vivo infectivity, an adenovirus cDNA library can be easily applied to the identification of disease relevant genes and high throughput screening of drugs.

Fourth, the methods described herein can be used to efficiently produce a vector that can be less prone to mutation than vectors produced using conventional methods. Conventional transfection-based methods for producing adenovirus vectors typically can generate about 1-2 plaque 10 days after transfection. Thus, amplification to one 6 cm dish can require at least two weeks. Compared to these conventional methods, our new method can induce full cytopathic effect in as little as two days after transfection. Also, since the batch does not depend on one starting plaque, our method is less prone to mutation of the clone. Thus, our method can permit one to more rapidly produce vector and/or produce vector that is less prone to mutation.

Construction of a Rescue Adenovirus

Figure 2A:
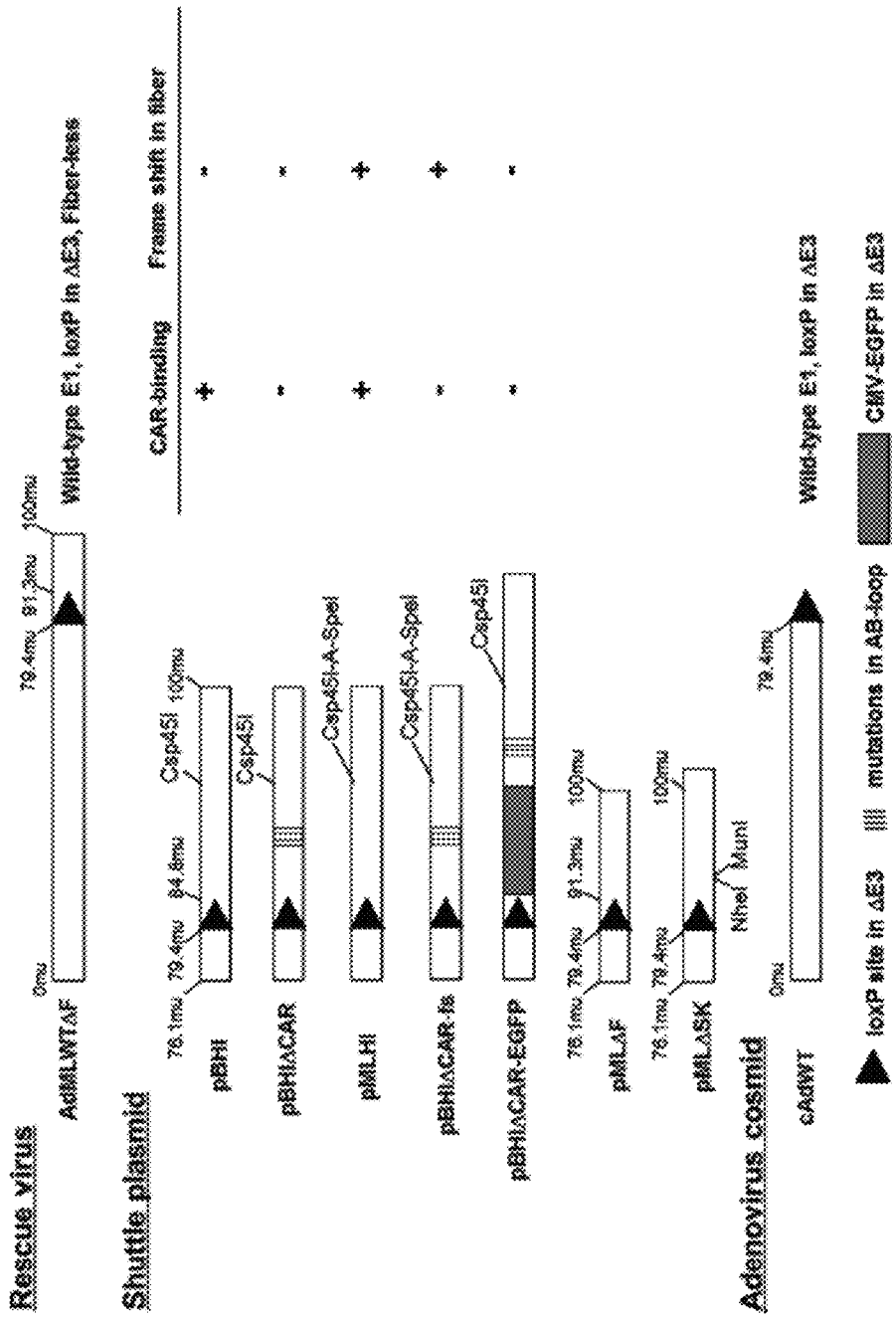
FIG. 2. Design of rescue virus, shuttle plasmid, and producer cells for recombinant adenovirus vector. Schematic presentation of adenoviral cosmids and fiber-modified shuttle plasmids. A single copy of a loxP sequence is substituted for the E3 gene (79.4-84.8 m.u.). The rescue virus has a wild-type E1 gene and a single loxP site at the E3 and fiber region deleted (79.4-91.3 m.u.). The DNA from the rescue virus was recombined with shuttle plasmid in adenovirus producer cell lines. (a) rescue virus, shuttle plasmid, and adenovirus cosmid constructs; (b) Wild-type HI loop sequence, background shuttle plasmid of HI-loop, fiber-modified library, and HI-loop random mutation fiber-modified library; (c) Wild-type AB-loop sequence and random mutations library.

The rescue virus, AdMLWTΔF (FIG. 2(a)), is a fiberless adenovirus with pseudo-typed fiber, and was constructed by in vitro Cre recombination in a fiber-complementing cell line. The fiberless adenoviral shuttle plasmids, pMLΔF, includes 76.1-100 map unit (m.u.) of the adenoviral genome with a single loxP site at the E3 and a deletion of the fiber region (79.4-91.3 m.u.). The pMLΔF was recombined with cAD-WT to generate fiberless adenovirus AdMLWTΔF in vitro by Cre. After the recombination, the recombinant DNA was transfected to 644 cells, which express chimeric adenovirus fiber protein (adenovirus type 5 tail and shaft, and adenovirus type 3 knob), so that the vector can be pseudo-typed and propagated in the 644 cells.

Construction of an HI-loop-modified Shuttle Plasmid Library

Figures 2B, 2C:

HI-loop fiber-modified adenovirus library was described in detail in Miura et al., Gene Ther. 2007 Oct.; 14(20):1448-60. Adenovirus libraries were based on the library backbone plasmids (pBMLHI and pBHIΔCAR-fs(+)) to display a random seven amino acid residue peptide on the HI-loop of the fiber knob domain. To generate HI-loop fiber-modified shuttle plasmid libraries, the degenerate oligonucleotide 5'-AACGGTACACAGGAAACAGGAGACA CAACT TTCGAA(NNK)$_7$ACTAGTCCAAGTGCATACTCTATGT-CATTTCATGG-3' (N=A, T, G or C; K=G or T; SEQ ID NO:1) served as a template for PCR with the primers 5'-GAAAC AGGAGACACAACTTTCGAA-3' (SEQ ID NO:2) and 5'-CATAGAGTATGCACTTGGACTAGT-3' (SEQ ID NO:3). The PCR product was digested with Csp45I and SpeI (restriction sites underlined) and ligated into the same sites of pMLHI and pBHIΔCAR-fs(+) and transfected into ElectroMax DH5α-E electrocompetent cells (Invitrogen, Carlsbad, Calif.) by electroporation. The plasmid libraries constructed from pMLHI and pBHIΔCAR-fs(+) were designated as pMLHI-lib and pBHIΔCAR-lib, respectively. Both pMLHI-lib and pBHIΔCAR-lib contained 2×10$^8$ clones, excluding insertless and unsuitable clones. The complexity of plasmid libraries was estimated by the number of clones growing from a representative aliquot of the transformed bacteria on agar plates containing ampicillin. (FIG. 2(b)).

Construction of an AB-loop-modified Shuttle Plasmid Library

Adenovirus library with random mutations in AB-loop of the fiber knob was based on the backbone plasmid, pMLABΔSK. Two steps of PCR were performed to generate AB-loop-modified shuttle plasmid library. For the first step, three PCR products were prepared; The degenerate oligonucleotide 5'-AAGCTAACTTTGTGGACCACACCA-GCTCCATCTCCTAA C(NNK)$_7$GATGCTAAACT-CACTTTGGTCTTAACAAAATGTGGCAGT-3' (N=A,T,G or C; K=G or T; SEQ ID NO:4) served as a template for PCR with the primers 5'-AAGCTAACTTT GTGGACCAC-3' (SEQ ID NO:5) and 5'-ACTGCCACATTTTGTTAAGA-3' (SEQ ID NO:6). For the upper PCR product (709bp), adenovirus type 5 genome served as a template for PCR with the primers 5'-AATTGCTAGCCCTGCAAACATCAG-3' (AB-upper S, SEQ ID NO:7) and 5'-GGTCCACAAAGT-TAGCTTATC-3' (SEQ ID NO:8). For the lower PCR product (442 bp), adenovirus type 5 genome served as a template for PCR with the primers 5'-TTAACAAAATGT GGCAGT-CAA-3' (SEQ ID NO:9) and 5'-AATTCAATT-GAAAAATAAACACGTTGAA-3' (AB-lower AS, SEQ ID NO:10).

These three PCR products, which were mixed with the equal mol ratio (upper PCR: library PCR: lower PCR=1:5:2), were used for the template for first step PCR without primers. In total, 26 cycles of PCR were carried out as follows 96° C. for 5 seconds, 52° C. for 5 seconds, 68° C. for 45 seconds without primers.

The second round of PCR was carried out using a first round PCR product for the template with the primers AB-upper S and AB-lower AS in 50 µl PCR solution containing 1.5 mM MgCl$_2$, 0.2 mM dNTPs, 1U of recombinant Taq polymerase. In total, 30 cycles of PCR were carried out as follows: 96° C. for 5 seconds, 64° C. for 5 seconds, and 68° C. for 45 seconds.

The final PCR product was digested with NheI and MunI, and then ligated into the same sites of pMLΔBASK and transfected into ElectroMAX DH5α-E electrocompetent cells (Invitrogen, Carlsbad, Calif.) by electroporation. The plasmid library constructed from pMLABΔSK was designated as pMLAB-lib. The pMLAB-lib contained 3×10$^8$ clones, excluding insertless and unsuitable clones. The complexity of plasmid libraries was estimated by the number of clones growing from a representative aliquot of the transformed bacteria on agar plates containing ampicillin (FIG. 2(c)).

Development of Basic Constructs for Generating Recombinant Adenovirus Vector.

To establish a basic construct for generating recombinant adenovirus vector, we first examined whether the vectors could be produced by a Cre-lox recombination system in producer cells between a fiber-modified shuttle plasmid and adenoviral DNA from the rescue virus with fiber-complementing. (FIG. 1). For gene recombination, approximately 1×10$^6$ 293-CRE cells or 293-CRE-69 cells were infected with 10,000 vp/cell of rescue virus, AdMLWTΔF, for two hours in a 6-cm culture dish. After 24 hours incubation at 37° C., cells were transfected with 5 µg of the shuttle plasmid with fiber-coding region. After 48 hours of transfection, cells were harvested by scraping and the crude viral lysate (CVL) was eluted by 3-4 freeze per thaw cycles. First, the pBHI(Csp), CAR-binding positive shuttle plasmid, was transfected into 293-CRE cells, which had been infected with rescue virus, AdMLWTΔF, 24 hours before the transfection. Adenoviral cytopathic effect (cpe) were clearly detected four days after the transfection.

We next confirmed whether the fiber-complement system could propagate fiber-modified adenovirus vector using pBHIΔCAR(Csp) and pMLHI. In 293-CRE-69 cells, clear cytopathic effects were detected with CAR-binding negative plasmid and reading frame-shifted plasmid at day 4, and half of cells were dead after the infection of pseudo-typed fiberless adenovirus. In 293-CRE cells, however, no cytopathic effects were detected at day 7 with these fiber-modified shuttle plasmids. (Table 1).

TABLE 1

Rescue of fiber-modified adenovirus vector independent of CAR-binding

| | Fiber modifications | | | |
|---|---|---|---|---|
| Cells | wt | CAR-binding(−) | Reading frame shifted | Fiberless |
| 293-CRE Fiber-expressing(−) | + | − | − | − |
| 293-CRE-69 Fiber-expressing(+) | + | + | + | ++ |

+: clear cpe were detected at Day 4
−: no cpe were detected at Day 7
++: clear cpe were observed at Day 2

Figure 3:
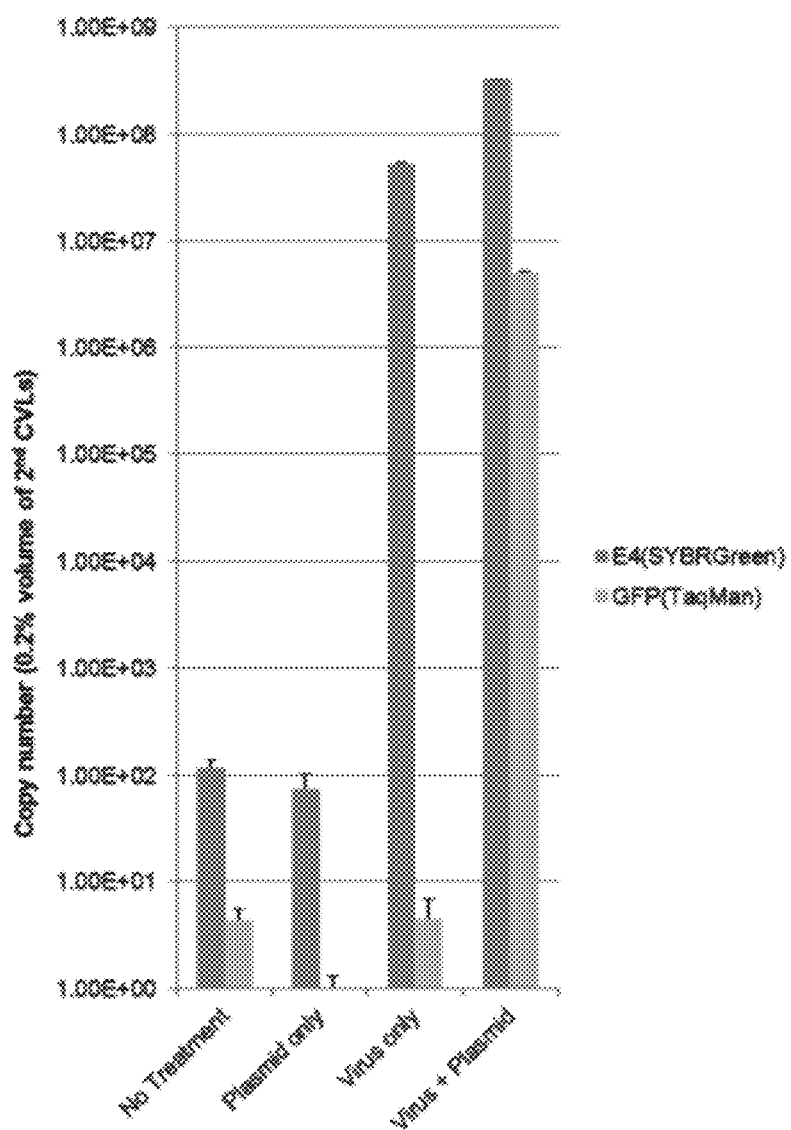
FIG. 3. Efficiency of recombinant adenovirus production. The efficiency of generating recombinant adenovirus vector was examined by quantitative PCR. 5 μg of pBHIDCAR-GFP were transfected into 293-CRE-69 cells after the infection of AdMLWTDF at 10,000 vp/cell. Two days after the transfection, first crude viral lysates were collected and 10% volumes of the first crude viral lysates were used to infect HEK293 cells. 24 hours after the HEK293 infection, second crude viral lysates were collected and 10% volumes of the second crude vial lysates were treated with DNaseI. 0.2% of the first crude viral lysates were analyzed by qPCR with E4 primers (SYBRGreen) for the total virus copy number and GFP-probe (TAQMAN Probe) for the recombinant viral copy number.

We then examined the efficiency of generating recombinant adenovirus vector. 5 µg of pBHIΔCAR-GFP were transfected into 293-CRE-69 cells after the infection of AdMLWTΔF at 10000 vp/cell. Two days after the transfection, first crude viral lysates were collected and 10% volumes of the first crude viral lysates were infected to HEK293 cells. 24 hours after the infection, second crude viral lysates were collected and 10% volumes of the second crude viral lysates were treated with DNaseI. After extracting DNA, 2% volumes of the second crude viral lysates (the equivalent of 0.2% of first crude viral lysates) were analyzed by quantitative PCR with E4 primers for the total virus copy number and GFP Probe for the recombinant viral copy number. There were, at minimum, $5 \times 10^6$ copies in 0.2% of first crude viral lysates, so that the vector generation from this method was $10^9$ copies in single 6-cm culture dish. (FIG. 3)

Production of a Fiber-modified Adenovirus Library

Figure 4:
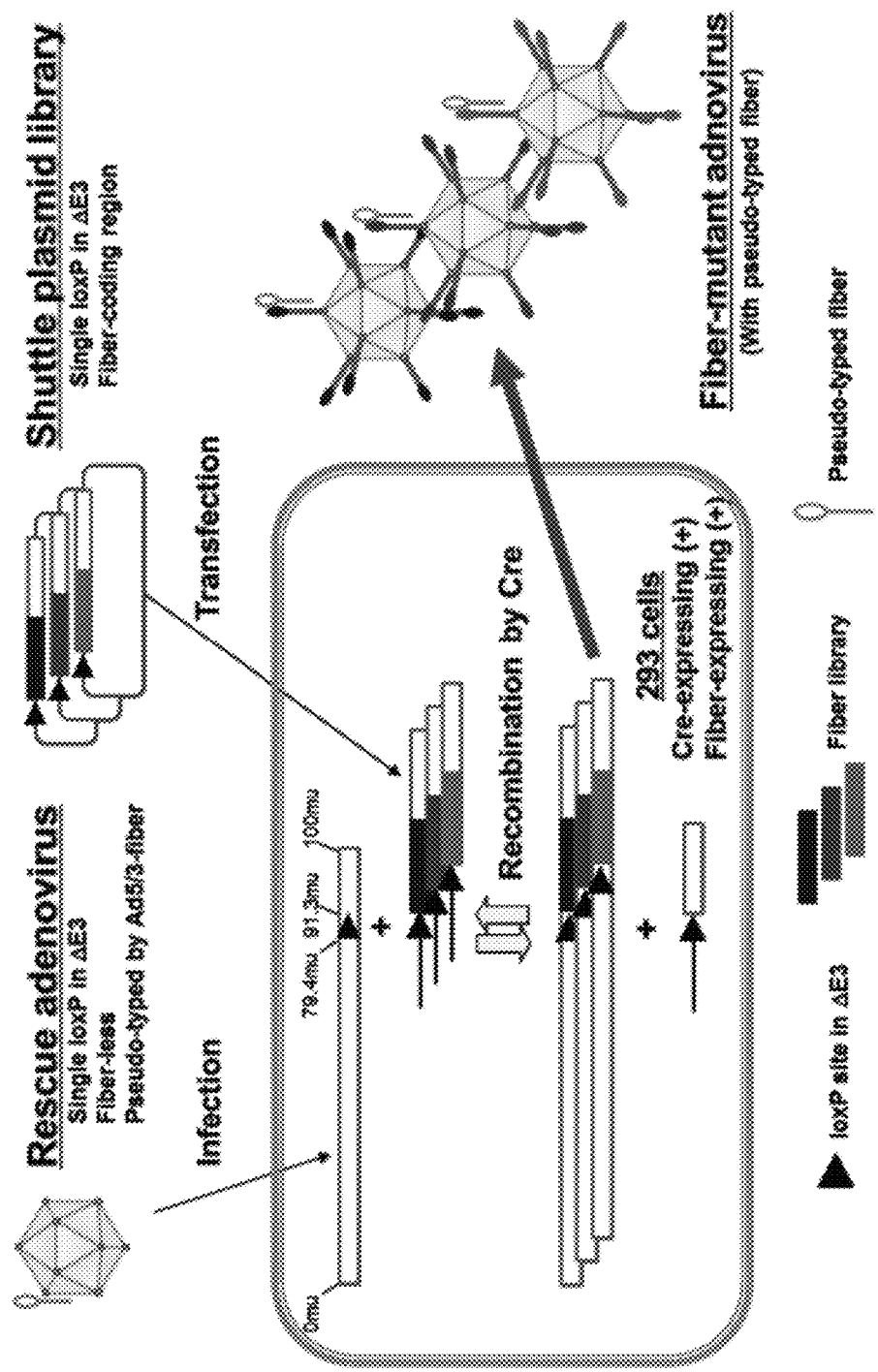
FIG. 4. Strategy for constructing fiber-mutant adenovirus library. The fiber-modified plasmid library was transfected into 293-CRE-69 cells, which had been infected with the rescue virus 24 hours before and 48 hours after the transfection, the first generation of the adenovirus library was produced.

The fiber modified plasmid libraries, pMLHI-lib and pBHIΔCAR-lib, were transfected into 293-CRE-69 cells, which had been infected AdMLWTΔF 24 hours before. Then, the genome from the rescue virus AdMLWTΔF was recombined with shuttle plasmid library in 293-CRE-69 cells by Cre. Forty-eight hours after the transfection, the first generation of the adenovirus library was produced. (FIG. 4). Since direct transfer of the adenoviral DNA from shuttle plasmid library into 293-CRE-69 cells might lead to an uptake of more than one library DNA per cell, the packaged adenovirus genome may not encode the peptide displayed on the fiber knob, impeding the selection process and subsequent identification of the library clone. In the first generation library, each adenovirus was pseudo-typed with Ad5/3 fiber, which enables one to start screening at the wide types of targeting cell. Additionally, at the beginning of screening, using the infection of the first-generated library to the targeting cells at a low multiplicity of infection avoids this problem. The virus production efficiency was highly improved by optimizing several factors such as, for example, the timeline of rescue-virus infection and shuttle plasmid transfection, the titer of rescue virus, the concentration of shuttle plasmid library.

Figure 5A:
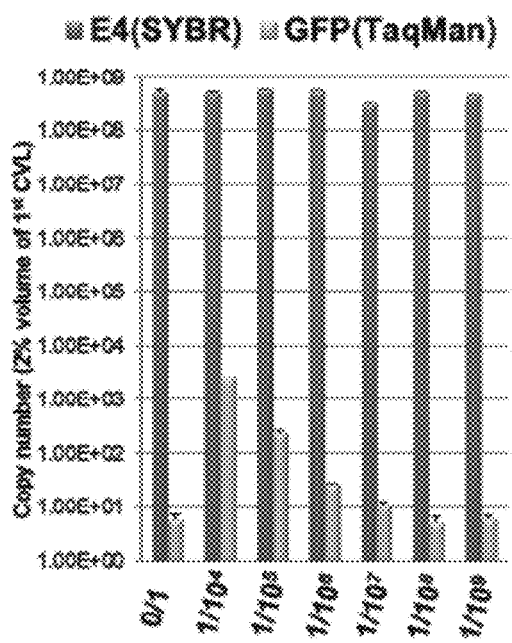
FIG. 5. Efficiency of EGFP-expressing adenovirus production from fiber-modified adenovirus library. Dilution experiments with shuttle plasmid library and shuttle plasmid expressing GFP. (a), (b) HI-loop modified library. The pBHIΔCAR-GFP were mixed with pBHIΔCAR-lib at various ratios (1:1×10$^4$, 1:1×10$^5$, 1:1×10$^6$, 1:1×10$^7$, 1:1×10$^8$, and 1×10$^9$), and transfected with the rescue virus into 293-CRE-69 cells. (c), (d) AB-loop modified library. The pBHIΔCAR-GFP were mixed with pMLAB-lib at various ratios (1:1×10$^4$, 1:1×10$^5$, 1:1 ×10$^6$, 1:1×10$^7$, 1:1×10$^8$, and 1×10$^9$), and transfected with the rescue virus into 293-CRE-69 cells. The CVL were collected two days after the transfection, 2% volumes of the crude viral lysates were treated with DNaseI, the viral DNA was extracted, and then subjected to quantitative PCR. Total viral copy numbers were determined by SYBRGreen with E4 primers; recombinant viral copy numbers were determined by TAQMAN Probe for GFP gene. Each bar represents the mean of three experiment ±SD. (a)(c) logarithmic scale. (b)(d) actual number.
Figure 5B:
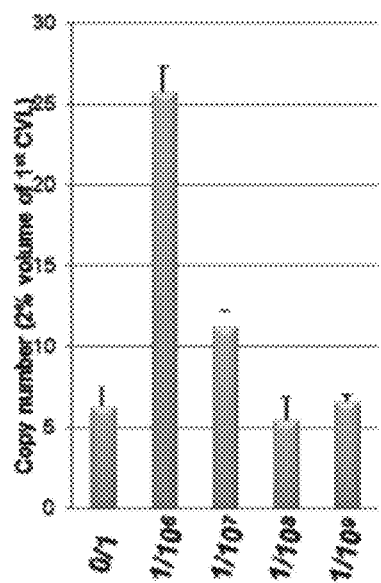
Figure 8B:
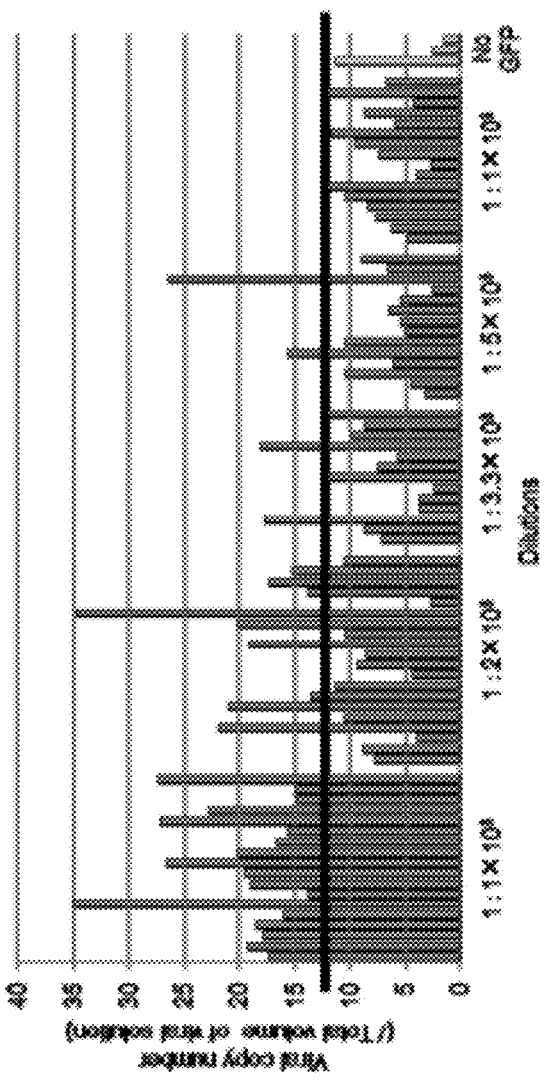
FIG. 8. In order to determine diversity, limit-dilution experiments with the shuttle plasmid library mixed with the GFP-coding shuttle plasmid were performed. A small amount of pBACΔR-GFP was mixed with pMLAB-lib at various ratios, and Ad libraries were generated from the mixtures. The viral DNA was extracted from the viral solution after treatment with DNaseI, and then recombinant viral copy numbers were determined by qPCR for GFP sequence. (a) When ½0amount of the viral solution was assessed, the GFP sequence coding virus was detected in a 4×10$^7$ dilution. (b) In order to assess the diversity more precisely, smaller steps of dilution were prepared for 1:1× 10$^8$ to 1×10$^9$, and virus library was produced as in (a).
Figure 8A:
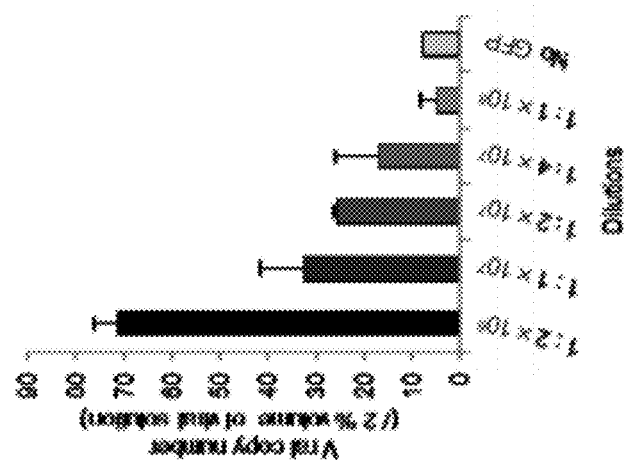

To estimate how many different adenoviruses in HI-loop library were produced by our rescue virus system, we set up dilution experiments with shuttle plasmid library and shuttle plasmid expressing GFP, the pBHIΔCAR-GFP, were mixed with pBHIΔCAR-lib at various ratios ($1:1 \times 10^4$, $1:1 \times 10^5$, $1:1 \times 10^6$, $1:1 \times 10^7$, $1:1 \times 10^8$, and $1 \times 10^9$), transfected with the rescue virus into 293-CRE-69 cells. After two days, 2% of the crude viral lysates were treated with DNaseI, the viral DNA was extracted, and then quantitative PCR was performed to determine total viral copy numbers and recombinant viral copy numbers. Total viral copy numbers were determined by SYBRGreen with E4 primers; recombinant viral copy numbers were determined by TAQMAN Probe for GFP gene. GFP gene was detected in a dilution range of $2 \times 10^6$ to $4 \times 10^7$ (FIG. 8). The dilution experiment suggested that the diversity of the library includes more than $5 \times 10^8$ per 6-cm dish. (FIG. 5(a), (b)).

We then generated a library of AB-loop mutants. The AB-loop of the fiber knob includes CAR-binding domains. If an AB-loop mutant allows the display of peptides and/or the insertion of ligands, the AB-loop may be an effective binding motif-presenting region. Introducing mutations into the AB-loop can be problematic using conventional methods, however, because mutations in the AB-loop can produce adenoviral conformation changes.

Figure 5C:
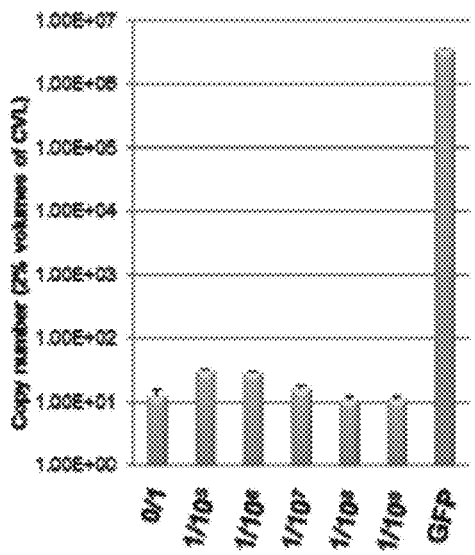
Figure 5D:
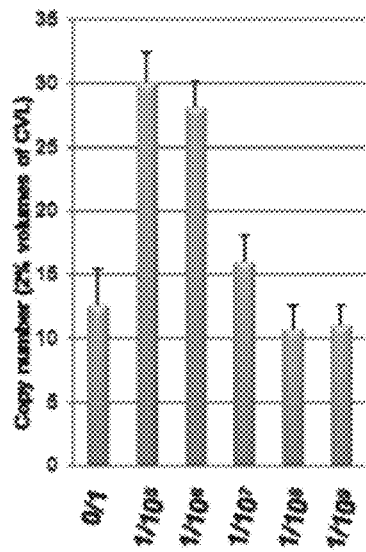

The new high-throughput library system described herein can provide a way to select new classes of adenovirus with AB-loop mutations. We performed dilution experiments for screening an adenovirus AB-loop mutant library with a shuttle plasmid library. A shuttle plasmid expressing GFP (pBHIΔCAR-GFP) was mixed with pMNAB-lib at various ratios ($1:1 \times 10^4$, $1:1 \times 10^5$, $1:1 \times 10^6$, $1:1 \times 10^7$, $1:1 \times 10^8$, and $\times 10^9$), then transfected with the rescue virus into 293-CRE-69 cells. After two days, 2% of the crude viral lysates were treated with DNaseI, viral DNA extracted, and then subjected to quantitative PCR to determine total viral copy number and recombinant viral copy number. Total viral copy numbers were determined by SYBRGreen with E4 primers; recombinant viral copy numbers were determined by TAQMANT Probe for the GFP coding region. GFP coding region was detected up to the $1 \times 10^7$ dilution, and five copies were existing in single 6-cm culture dish at minimum. The dilution experiment suggested that the diversity of the library includes more than $1 \times 10^9$ per 6-cm dish. (FIG. 5(c), (d)).

Figure 6:
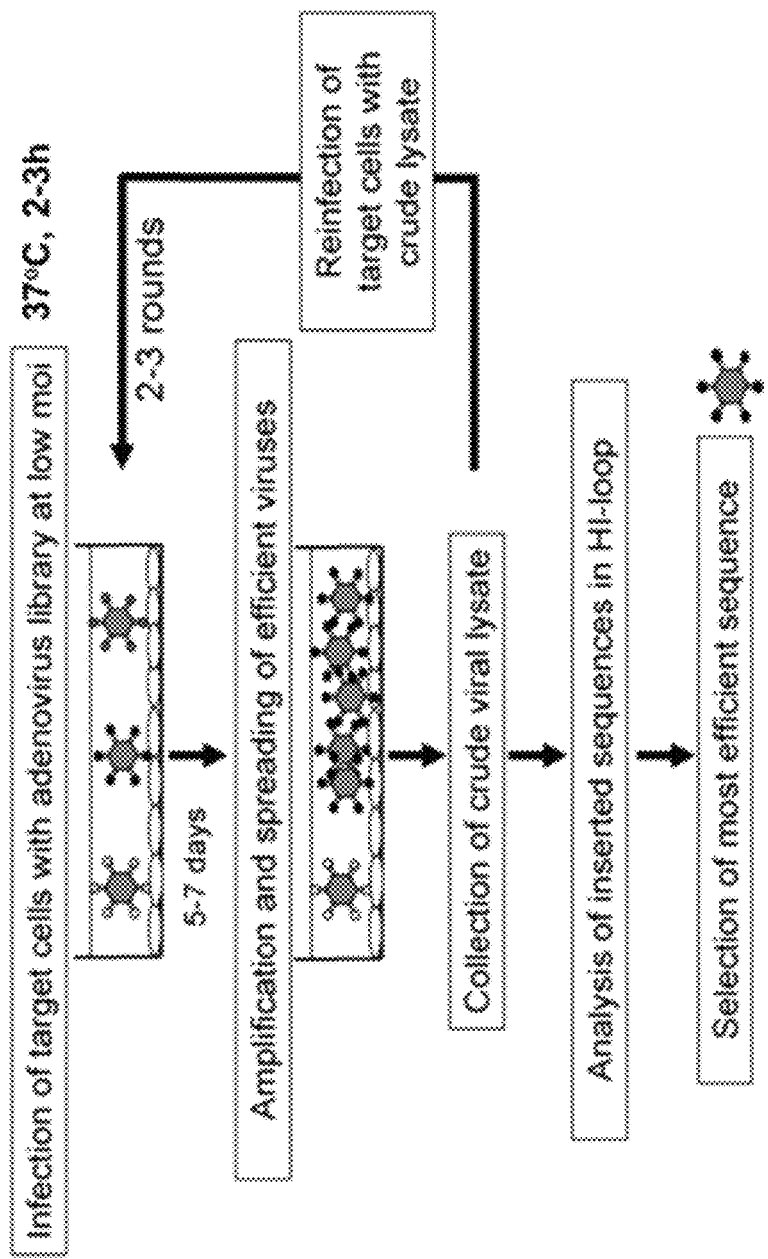
FIG. 6. Screening strategy of adenovirus library. First, the target cells were infected with the adenovirus library at a low multiplicity of infection. Next, the expanded adenoviruses are recovered from the cells and subjected to two or three more rounds of selection. The DNA region containing fiber-mutant of the selected adenoviruses is then analyzed.

Selection of AB-loop Fiber-Modified Adenovirus Library Clones Targeting Panc1 Cells To demonstrate that in vitro screening could produce modified-fiber adenovirus clones with high transduction efficiency to target cells, the Panc1 cell line was infected at an multiplicity of infection of 1 (FIG. 6). Since the library used in the screening was collected from ten 6-cm dishes, the theoretical diversity of the fiber-modified adenoviruses in the library was estimated to be approximately $1 \times 10^{10}$, and final concentration of the virus library was prepared as $5 \times 10^8$ vp/ml. Infection at such a low multiplicity of infection allows the average chance of adenovirus exposure to be less than one virus genome per cell, reducing the likelihood of a mismatch between the phenotype and the sequence coding in the adenovirus genome. In the initial phase of the screening, many low-affinity or nonspecific viruses might bind and internalize into the Panc1 cells because each virus was pseudo-typed. However, for the viruses presenting modified-fiber that matched modified adenoviral genome, using a replication-competent adenovirus could allow for the rapid spreading of the most efficient viruses in the library in following replication steps, thereby leading to an effective enrichment of such viruses. Amplified and expanded adenoviruses were recovered and subjected to three more rounds of selection. The DNA region containing the AB-loop mutant of adenovirus recovered from three rounds of selection was then amplified by PCR. DNA sequencing of the PCR products revealed enrichment of several candidates, and the most abundant consensus sequences after two rounds of selection were VTINRSA (SEQ ID NO:12) and THLSIYA (SEQ ID NO:14) (Table 2).

Characterization of Adenovirus with Selected Fiber

Figure 7A:
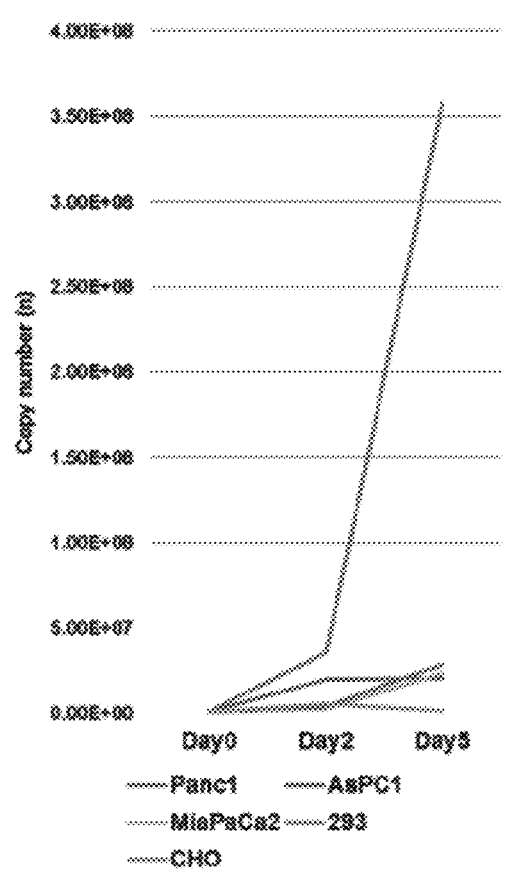
FIG. 7. Binding and replication assay of AB-mutants virus pool from the 3$^{rd}$ round screening on Panc1 cells. (a)Viral replication in Panc1 cells. Panc1 cells were infected with 0.1 vp/cell of the AB-mutants virus pool from the third round screening on Panc1 cells at 37° C. for two hours. Cells were harvested on Day 2 and Day 5 after the infection and then subjected to qPCR. 2% volumes of the crude viral lysates were treated with DNaseI, the viral DNA extracted, and then subjected to quantitative PCR, which detected total viral copy numbers by SYBRGreen with E4 primers. (b)Viral binding to Panc1 cells. 100 vp/cell of the AB-mutants virus pool from the third round screening on Panc1 cells at 4° C. for two hours. Cells were harvested immediately after the infection and then subjected to qPCR. 2% volumes of the CVL were treated with DNaseI, the viral DNA extracted, and then subjected to quantitative PCR, which detected total viral copy numbers by SYBRGreen with E4 primers.
Figure 7B:
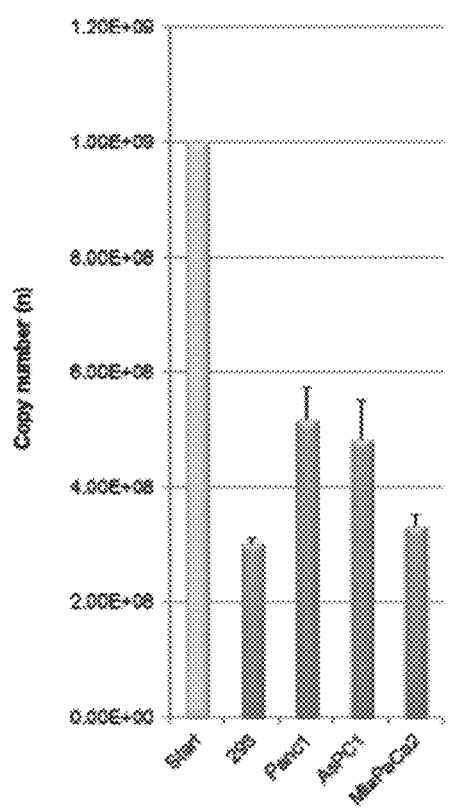

To test the binding and replication ability of the selected virus pool, we analyzed the copy number of AB-mutants virus pool from the third round of screening on Panc1 cell line by quantitative PCR (FIG. 7(a), 7(b)). The third virus pool was infected at 0.1 vp/cell at 37° C. for two hours into Panc1, AsPC1, MiaPaCa2, CHO, or HEK293 cells. The cells were intensively washed twice in PBS after the infection and incubated at 37° C. for either two days or five. Quantitative PCR was performed with the viral DNA from crude viral lysates. The quantitative PCR showed that replication ability of third virus pool was ten-fold higher in Panc1 cells than in other cell lines at day 5 (FIG. 7(a)). Next, to examine binding activity, the third virus pool was infected at 100 vp/cell at 4° C. for two hours into Panc1, AsPC1, MiaPaCa2, or HEK293 cells. The binding activity observed with Panc1 cells also was higher than that observed in the other cell lines (FIG. 7(b)). Since the replication of this virus pool in

TABLE 2

AB-loop mutant sequences from adenovirus library on Panc1 cells

| Initial Library | Selection Round | | |
|---|---|---|---|
| | 1 | 2 | 3 |
| AAWV (SEQ ID NO: 26) | CSLNGGG (SEQ ID NO: 41) | THLSIYA (SEQ ID NO: 14) | THLSIYA (SEQ ID NO: 14) |
| AMYSTLY (SEQ ID NO: 27) | EGRRVGG (SEQ ID NO: 42) | THLSIYA (SEQ ID NO: 14) | THLSIYA (SEQ ID NO: 14) |
| DARVD*D (SEQ ID NO: 28) | ETSSLLF (SEQ ID NO: 43) | THLSIYA (SEQ ID NO: 14) | VTINRSA (SEQ ID NO: 12) |
| FLAFCFA (SEQ ID NO: 29) | GGREKKD (SEQ ID NO: 44) | THLSIYA (SEQ ID NO: 14) | VTINRSA (SEQ ID NO: 12) |
| IHSALRA (SEQ ID NO: 30) | NKAHFGN (SEQ ID NO: 45) | VTINRSA (SEQ ID NO: 12) | VTINRSA (SEQ ID NO: 12) |
| IRVWK*I (SEQ ID NO: 31) | SSILWIG (SEQ ID NO: 46) | VTINRSA (SEQ ID NO: 12) | VTINRSA (SEQ ID NO: 12) |
| IYYTIST (SEQ ID NO: 32) | TGACSWS (SEQ ID NO: 47) | VTINRSA (SEQ ID NO: 12) | VTINRSA (SEQ ID NO: 12) |
| NRRTILM (SEQ ID NO: 33) | THLSIYA (SEQ ID NO: 14) | VTINRSA (SEQ ID NO: 12) | VTINRSA (SEQ ID NO: 12) |
| PGAGWRP (SEQ ID NO: 34) | THLSIYA (SEQ ID NO: 14) | VTINRSA (SEQ ID NO: 12) | VTINRSA (SEQ ID NO: 12) |
| RNNDDTL (SEQ ID NO: 35) | THLSIYA (SEQ ID NO: 14) | VTINRSA (SEQ ID NO: 12) | VTINRSA (SEQ ID NO: 12) |
| RVSRNRL (SEQ ID NO: 36) | THLSIYA (SEQ ID NO: 14) | | |
| SERGDWA (SEQ ID NO: 37) | THLSIYA (SEQ ID NO: 14) | | |
| VEVGGGW (SEQ ID NO: 38) | THLSIYA (SEQ ID NO: 14) | | |
| WGAVFGG (SEQ ID NO: 39) | THLSIYA (SEQ ID NO: 14) | | |
| WHHCPYS (SEQ ID NO: 40) | THLSIYA (SEQ ID NO: 14) | | |
| | VGAWTGR (SEQ ID NO: 48) | | |
| | VYPTHGK (SEQ ID NO: 49) | | |

HEK293 cells, which express CAR at a higher level than do than Panc1 cells, was pretty low, these results suggest that these mutant motifs in AB-loop might inhibit native tropism, contributing to the targeting nature of the virus.

Isolation of AB-loop-modified Adenoviral Clones for Mesothelin Targeting

Figure 9:
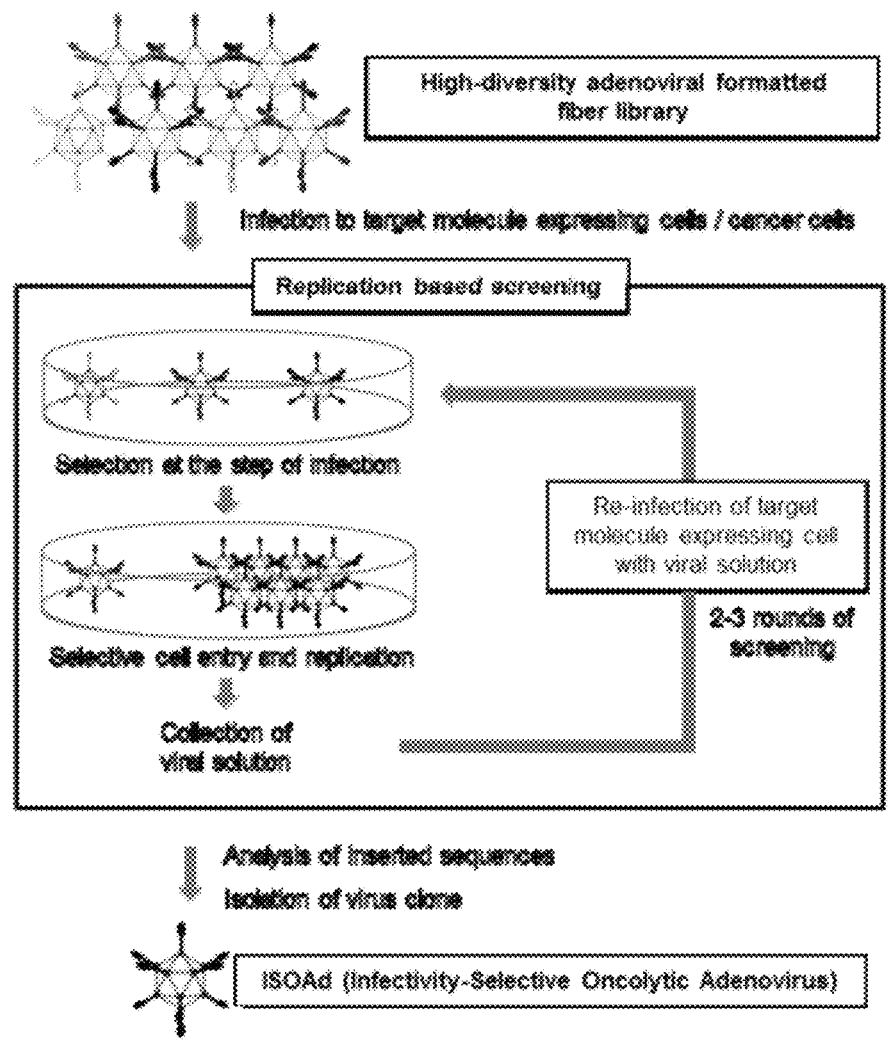
FIG. 9. High-throughput screening of the adenovirus library in the AB-loop for mesothelin (MSLN) expressing cells. Via the replication-based high-throughput screening, the Infectivity-Selective Oncolytic Ad Adenovirus (ISOAd) was isolated from a high diversity Ad library of targeting motifs based on transduction and subsequent replication. First, the target cells were infected with the Ad library at a low multiplicity of infection (MOI). After 5-7 days, the amplified Ads were recovered from the cells and subjected to a few more rounds of re-infection. The viral solution from each round was harvested and the sequences of the targeting motifs were analyzed. The DNA sequences of the AB-loop region of the Ads screened with 293-MSLN cells were amplified by PCR and analyzed after cloning into a plasmid. While the initial library sequence was completely diverse, screening after virus amplification in 293-MSLN cells started to show convergence of the targeting motif sequences as early as the first round of screening. After subsequent rounds of screening, the sequence further converged eventually to a single clone (VTINRSA, SEQ ID NO:12).

Next, we used mesothelin (MSLN) as a target cell-surface molecule for library screening. MSLN may be overexpressed in, for example, pancreatic cancer, ovarian cancer, and malignant mesothelioma, while little or no expression is typically detected in normal tissues. In order to isolate a MSLN-targeting adenovirus, we established the 293 cells over-expressing MSLN (293-MSLN), and the library screening was performed with this cell line by replication-based selection (FIG. 9). Since the library used in the screening was collected from ten 6-cm dishes, the library diversity of the fiber-modified adenoviruses was considered to be $5 \times 10^9$. In each round, the DNA was extracted from viral solution and the region corresponding to the AB-loop of adenovirus was sequenced after being cloned into the plasmid. The convergence of the sequence was observed as early as the first screening round and the VTINRSA (SEQ ID NO:12) sequence became dominant after the second round (Table 3).

TABLE 3

AB-loop mutant sequences from adenovirus library on 293-MSLN cells

| Initial Library | Selection Round | | |
|---|---|---|---|
| | 1 | 2 | 3 |
| AAWV (SEQ ID NO: 26) | THLSIYA (SEQ ID NO: 14) | THLSIYA (SEQ ID NO: 14) | VTINRSA (SEQ ID NO: 12) |
| AMYSTLY (SEQ ID NO: 27) | THLSIYA (SEQ ID NO: 14) | THLSIYA (SEQ ID NO: 14) | VTINRSA (SEQ ID NO: 12) |
| DARVD*D (SEQ ID NO: 28) | THLSIYA (SEQ ID NO: 14) | VTINRSA (SEQ ID NO: 12) | VTINRSA (SEQ ID NO: 12) |
| FLAFCFA (SEQ ID NO: 29) | THLSIYA (SEQ ID NO: 14) | VTINRSA (SEQ ID NO: 12) | VTINRSA (SEQ ID NO: 12) |
| IHSALRA (SEQ ID NO: 30) | THLSIYA (SEQ ID NO: 14) | VTINRSA (SEQ ID NO: 12) | VTINRSA (SEQ ID NO: 12) |
| IRVWK*I (SEQ ID NO: 31) | THLSIYA (SEQ ID NO: 14) | VTINRSA (SEQ ID NO: 12) | VTINRSA (SEQ ID NO: 12) |
| IYYTIST (SEQ ID NO: 32) | THLSIYA (SEQ ID NO: 14) | VTINRSA (SEQ ID NO: 12) | VTINRSA (SEQ ID NO: 12) |
| NRRTILM (SEQ ID NO: 33) | THLSIYA (SEQ ID NO: 14) | VTINRSA (SEQ ID NO: 12) | VTINRSA (SEQ ID NO: 12) |
| PGAGWRP (SEQ ID NO: 34) | VTIDRSA (SEQ ID NO: 50) | VTINRSA (SEQ ID NO: 12) | VTINRSA (SEQ ID NO: 12) |
| RNNDDTL (SEQ ID NO: 35) | VTINRSA (SEQ ID NO: 12) | VTINRSA (SEQ ID NO: 12) | VTINRSA (SEQ ID NO: 12) |
| RVSRNRL (SEQ ID NO: 36) | VTINRSA (SEQ ID NO: 12) | | |
| SERGDWA (SEQ ID NO: 37) | VTINRSA (SEQ ID NO: 12) | | |
| VEVGGGW (SEQ ID NO: 38) | VTINRSA (SEQ ID NO: 12) | | |
| WGAVFGG (SEQ ID NO: 39) | VTINRSA (SEQ ID NO: 12) | | |
| WHHCPYS (SEQ ID NO: 40) | VTINRSA (SEQ ID NO: 12) | | |
| | VTINRSA (SEQ ID NO: 12) | | |
| | VTINRSA (SEQ ID NO: 12) | | |
| | VTINRSA (SEQ ID NO: 12) | | |

Binding of the Isolated Adenovirus Clone to Mesothelin

Figure 10A:
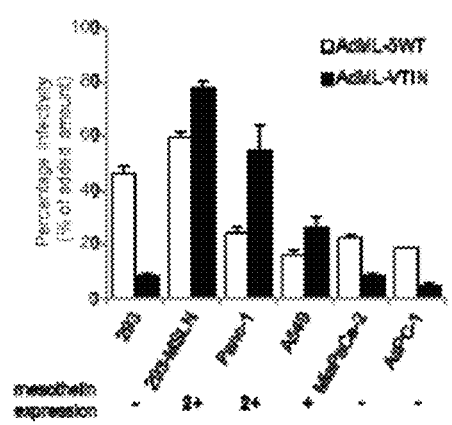
FIG. 10. Binding of the isolated adenovirus clone to mesothelin. (a) Binding ability of AdML-VTIN correlated well with mesothelin (MSLN) expression in various cell lines (293, 293-MSLN, Panc-1, A549, MiaPaCa-2, and AsPC-1). Binding of AdML-5WT (control Ad with a wild type fiber) did not correspond to the MSLN level. The isolated total DNA was analyzed by the E4 qPCR to determine the adenoviral copy number bound to the surface of the cells. The level of MSLN expression was determined by flow-cytometry (shown below the graph). (b) Flow-cytometry of cell surface mesothelin. Expression of mesothelin was determined by flow-cytometry. Shaded: without anti-mesothelin antibody, Black-line; with anti-mesothelin antibody. (c) Suppression of MSLN expression with the anti-MSLN siRNA eliminated AdML-VTIN binding to the target cells (: P<0.01, *: P<0.001). (d) Pre-treatment with the anti-MSLN antibody (two hours at 4° C.) significantly reduced binding of AdML-VTIN to the MSLN-positive target cells.
Figure 10B:
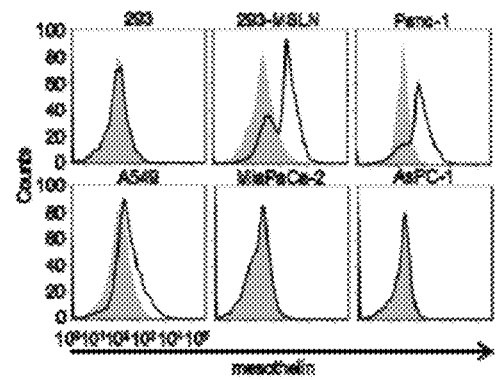
Figure 10C:
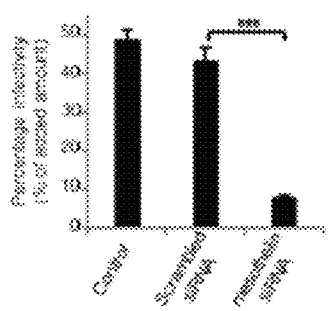
Figure 10D:
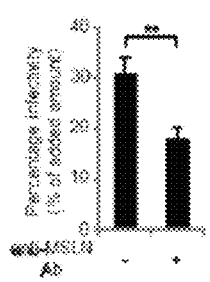

When binding of the isolated adenovirus with the VTINRSA (SEQ ID NO:12) motif (AdML-VTIN) was analyzed in 293, 293-MSLN, Panc-1, A549 and MiaPaCa-2, it corresponded to the level of cell surface MSLN-expression analyzed by flow-cytometry (FIG. 10a, b). In particular, binding of AdML-VTIN to 293-MSLN cell (showing highest MSLN expression) was significantly higher than that in any other cells. In order to further confirm the role of MSLN for AdML-VTIN infection, we analyzed the effect of MSLN inhibition on the binding of AdML-VTIN by employing siRNA and antibody against MSLN. The anti-MSLN siRNA almost completely suppressed AdML-VTIN binding to MSLN-expressing cells, 293-MSLN (FIG. 10c and FIG. 11a) and Panc-1 (FIG. 10b). The anti-MSLN antibody also significantly inhibited the binding of AdML-VTIN to 293-MSLN (FIG. 10d). This data indicated that MSLN was a receptor moiety for AdML-VTIN and provided an important evidence showing functionality of our high-throughput large-library screening for identification of the selective targeting moiety binding against the specific cell surface molecule of the target cells.

Characterization of the Identified Infectivity-Selective Oncolytic Adenovirus (ISOAd)

Figure 12A:
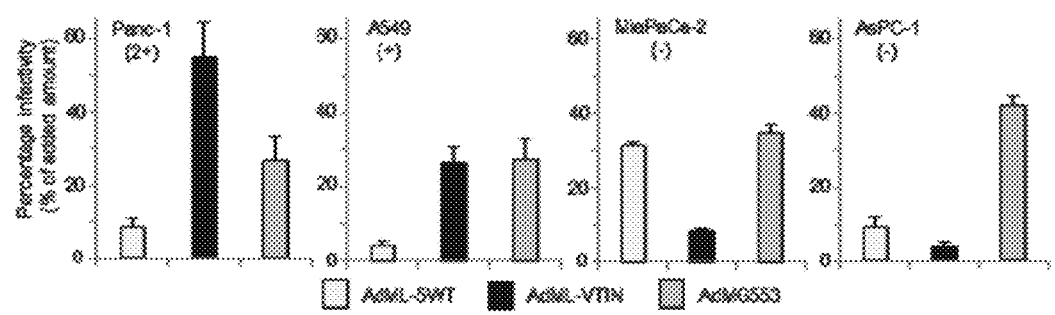
FIG. 12. Characterization of the newly isolated adenovirus AdML-VTIN. (a) The analysis of infectivity demonstrated that the MSLN-targeted AdML-VTIN outperformed not only the control Ad with a native fiber (AdML-5WT) but also the infectivity-enhanced Ad with an Ad5/Ad3-fiber (AdMG553) in MSLN strongly-positive Panc-1. In MSLN-intermediately positive A549 cells, the infectivity of AdML-VTIN was as high as that with AdMG553. However, its binding to MSLN-negative MiaPaCa-2 and AsPC-1 cells was significantly lower than other vectors. (b) AdML-VTIN showed exponential amplification selectively in MSLN positive cells (Panc-1 and A549), and the extent of virus burst corresponded with the MSLN level of each cell line. The result was shown as a virus burst size (vp/cell) (n=3). Mesothelin expression: strong (2+), moderate (+), low (−).
Figure 12B:
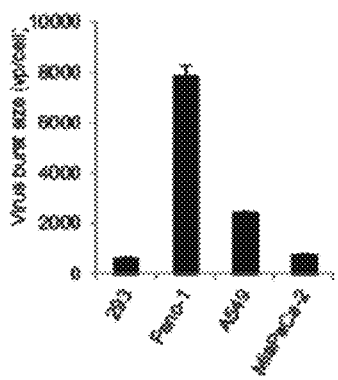

The newly identified transductionally-retargeted ISOAd (AdML-VTIN) was compared to the control adenoviruses with either the native Ad5 fiber (AdML-5WT) or the infectivity-enhanced Ad5/Ad3 fiber (AdMG553) in the cell lines showing different levels of MSLN expression (FIG. 12a). In Panc-1 (MSLN strongly-positive pancreatic cancer), the binding ability of the AdML-VTIN was 5-fold higher than that of AdML-5WT and twice as high as that of AdMG553. The binding ability in A549 (MSLN moderately-positive) was also higher than that of AdML-5WT. Conversely, AdML-VTIN binding to MiaPaCa-2 or AsPC-1 (MSLN negative) was as low as the background level. Importantly, the binding of AdML-VTIN to Panc-1 was stronger than that with the Ad5/Ad3 modified fiber which was reported to show the strongest infectivity in many CAR-negative cancer cells including pancreatic cancer. In the context of virus replication, AdML-VTIN showed exponential amplification selectively in MSLN-positive cells and the extent of virus burst corresponded with MSLN-expression of each cell line (FIG. 12b). Therefore, the VTINRSA (SEQ ID NO:12) motif was identified as the first genetically-coded Ad targeting motif with improved potency and selectivity.

Figure 13A:
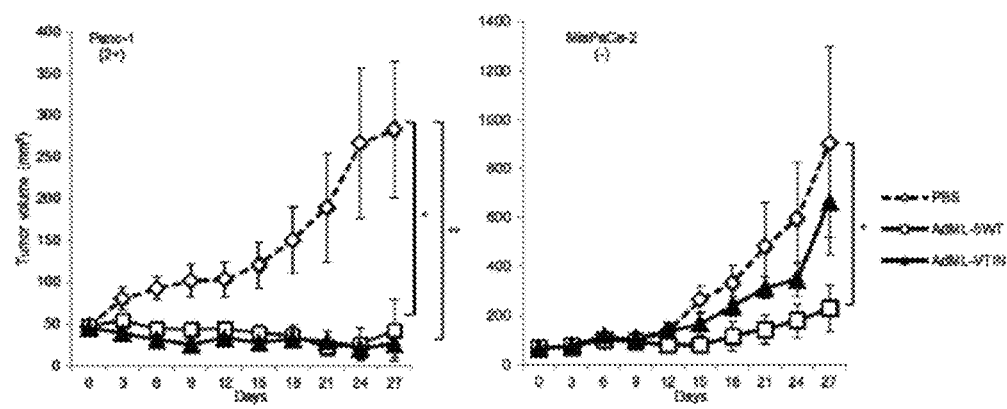
FIG. 13. In vivo anti-tumor effect and viral replication of the infectivity-selective oncolytic adenovirus (ISOAd). (a) The in vivo anti-tumor effect of the mesothelin-targeted AdML-VTIN was analyzed in Panc-1 (MSLN-positive) and MiaPaCa-2 (MSLN-negative) subcutaneous xenografts. AdML-VTIN showed a strong anti-tumor effect only in the MSLN expressing Panc-1 tumors, while the effect of AdML-5WT was not selective. Each symbol represents the mean of tumor volumes ±s.e.m. (n=4-8) (*: P<0.05, : P<0.01). (b) Five days after intratumoral injection of the viruses, the expression of an adenoviral late gene product (hexon) was assessed by immunostaining with the anti-hexon polyclonal antibody (counterstained with Hoechst 33342). Staining and sections were performed in at least two independent experiments. Green: adenovirus hexon protein, Blue: nucleus (original magnification: 100). (c) The viral copy numbers in the DNA isolated from tumor specimens at day 5 were analyzed by qPCR. The result is shown as the adenoviral copy number per 1 ng DNA. (*: P<0.005) Mesothelin expression: strong (2+), moderate (+), low (−).

In Vivo Anti-tumor Effect and Virus Replication of Transductionally-retargeted Oncolytic Adenovirus The in vivo therapeutic effect of the MSLN-retargeted oncolytic Ad was analyzed in Panc-1 (MSLN-positive) and MiaPaCa-2 (MSLN-negative) pancreatic cancer subcutaneous xenografts (FIG. 13a). When tumors reached 5-7 mm, $10^{10}$ vp of AdML-VTIN or AdML-5WT were injected intratumorally. The MSLN-targeted virus (AdML-VTIN) exhibited significant tumor volume reduction in MSLN-positive Panc-1 xenografts (P=0.006 vs. PBS-treated control), while it did not show anti-tumor effect in MSLN-negative MiaPaCa-2 tumors. Disappearance of tumors was observed only in the Panc-1 xenografts treated with the MSLN-targeted AdML-VTIN virus (4 out of 8 mice).

Figure 13B:
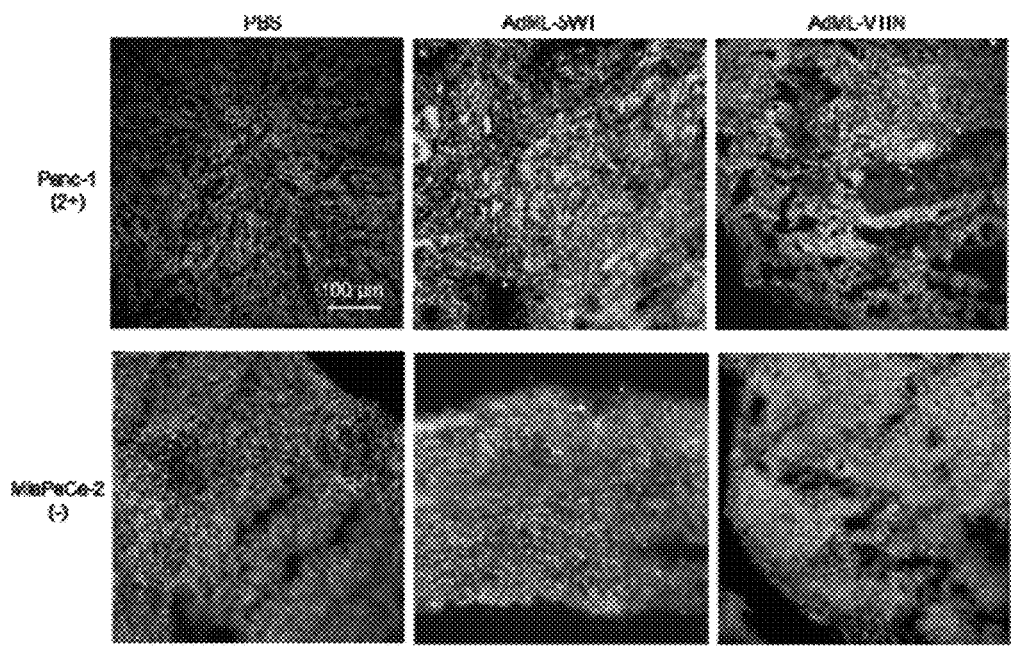

To investigate replication and intratumoral spread of the virus, we performed a separate experiment with the same setup and stained the tumor specimens for the virus structural protein, hexon, five days after infection. After treatment with AdML-VTIN, a majority of the cells in the Panc-1 tumors expressed high level of hexon protein, while there were few low-intensity hexon-positive cells in MiaPaCa-2 specimens. The non-targeted virus, AdML-5WT, resulted in moderate level of hexon expression in both Panc-1 and MiaPaCa-2 xenografts. In MSLN-positive Panc-1 tumors, the hexon immunostaining signal with AdML-VTIN was remarkably higher than that with AdML-5WT (FIG. 13b).

Figure 13C:
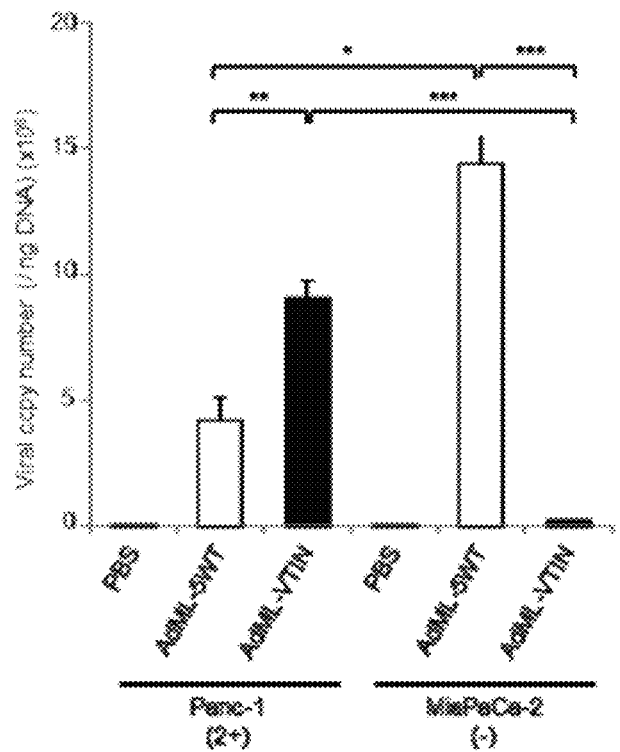

The virus copy number in the treated tumor was determined by qPCR with the primers for the Ad E4 region. In Panc-1, the virus copy number (Day 5) with AdML-VTIN was twice as high as that with AdML-5WT (P=0.002). In MiaPaCa-2, AdML-VTIN viral replication was significantly lower compared to AdML-5WT (P=0.00003). When virus replication was compared between MSLN-positive and negative xenografts, the copy number of AdML-VTIN was noticeably higher (40-fold) in Panc-1 than that in MiaPaca-2 (P=0.00003) (FIG. 13c). These data indicated the viral replication of MSLN-retargeted adenovirus correlates with the anti-tumor effect. These experiments confirmed the selectivity and potency of the oncolytic andenovirus with the VTINRSA (SEQ ID NO:12) as a targeting motif against MSLN-positive tumors.

In Vivo Distribution of the Novel Fiber-modified Virus After Systemic Administration.

Figure 14A:
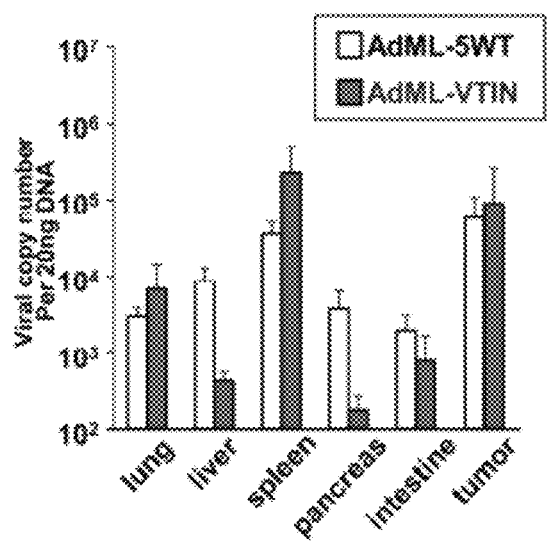
FIG. 14. In vivo distribution of the novel fiber-modified virus after systemic administration. A) 48 hours after injection. The novel fiber modified virus generated with our novel technique (AdML-VTIN) was injected into the tail vein of the mice. The virus distribution in the tumor and major organs was analyzed by virus DNA qPCR at 48 hours after injection. B) Virus distribution seven days after injection. The tumor distribution of the VTIN virus was more than three orders of magnitude higher than the wild type virus.
Figure 14B:
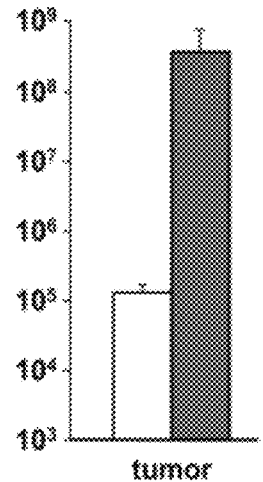

In vivo distribution of systemically administered virus was assessed in athymic nude mice with MSLN positive xenografts. When the Panc-1 tumor became 5-7 mm, $10^{11}$ vp of viruses with the MSLN-binding VTIN motif (AdML-VTIN) or $10^{11}$ vp of viruses with the wild type fiber (AdML-5WT) were injected respectively into the tail vein of the mice. The major organs were harvested 48 hrs after injection, and DNA was isolated form them. The qPCR analyses of virus sequence revealed decrease of the VTIN-virus distribution in most of the organs and increase in the tumor, compared to the virus with wild type fiber. Particularly, the decrease in the liver was significant and more than one order of magnitude (FIG. 14a). When the virus quantity in the tumor was compared after 7 days of injection, the quantity of VTIN virus was more than 3 orders of magnitude higher than that of wild type virus (FIG. 14b).

High throughput screening of a targeting ligand library in an adenovirus format can be an attractive way to develop infectivity-selective oncolytic adenoviruses. Achieving the required library size, however, has been extremely difficult due to certain virological barriers: (i) poor transfection efficiency of a large Ad-coding plasmid; (ii) insufficient recombination efficiency; and/or (iii) unintended restriction of the clones based on the infectivity in producer cells. The novel pseudotyped rescue virus system described herein is designed to circumvent one or more of these barriers. In order to reduce the possibility of having multiple copies of one clone in the library, we determined library diversity using a limit dilution assay. Our system reproducibly achieves a level of diversity of at least 5 $10^9$. A library of this size can allow screening of random amino acid sequences as long as at least seven amino acids, substantiating the use of adenovirus as an expression platform for biologically meaningful library screening.

Moreover, modifying adenovirus fiber for targeted in vivo distribution of the adenovirus following systemic administration has proven difficult using conventional methods due, at least in part, to difficulty successfully coding the targeting motif into the virus genome. The fiber-modified virus generated using our new method, however, can reduce unwanted sequestration of the virus in certain organs (e.g., liver and/or pancreas, see FIG. 14a) and increase virus distribution is, for example, tumor tissues. Thus, fiber-modified adenoviruses generated using the method described herein can allow targeted delivery of anti-tumor therapy.

The position into which the targeting motif is placed in the adenovirus may be important for successful targeting. The AB-loop of adenovirus fiber can shapes the CAR-binding domain and can mediate initial viral binding for infection.

However, mutations in the AB-loop can induce adenoviral conformation changes. Until now, therefore, attempts to construct adenoviral fiber-modified-library presented library peptides in the HI-loop of the fiber knob, which accepts a wide variety of inserts such as, for example, the RGD motif. In this work, we produced a large-size adenovirus library with targeting motifs successfully presented in the AB-loop of the adenovirus fiber knob region by exploiting a highly efficient vector generation system.

In order to prove the functionality of the library system and the high throughput screening, we performed a screening of the AB-loop adenoviral library for mesothelia. (MSLN) as a target. MSLN is a surface glycoprotein attached to the cell membrane by a glycosylphosphatidylinositol anchor and is postulated to function in cell adhesion. MSLN shows overexpression in many malignancies including, for example, pancreatic cancer, malignant mesothelioma, and ovarian cancer. Therefore, our MSLN-targeted vector has potential for application in many MSLN expressing cancers. Although a conditionally replicative Ad with the MSLN promoter-based control has been reported (Tsuruta Y et al., 2008, *Clin Cancer Res* 14:3582-3588), the fiber in this structure does not possess specificity to the target cancer cells, and thus the adenovirus is not selective at the step of infection. Such vectors experience sequestration by non-target organs and/or cells and may impose higher risk of toxicity because they may infect non-cancer cells. Therefore, targeting at the stage of infection is critical for circumventing the aforementioned issues both by increasing infection in cancer cells and decreasing the absorption of viral particles by non-target cells around the region. The target specificity and anti-tumor potency are attributes of fully functional oncolytic viruses.

The MSLN-targeted ISOAd (Infectivity-Selective Oncolytic Adenovirus) generated in this study with the newly identified targeting motif exhibited powerful infectivity of cancer cells overexpressing MSLN. Moreover, the oncolytic activity of the virus with this targeting motif was highly selective in vitro and in vivo. These data provide a foundation for a new category of cancer therapeutics, the infectivity-selective oncolytic virus. Our new library system is an innovative technology which enables the development of the ISOAd not only for the known target molecules but also for unknown surface molecules of intended target cancer cells.

In this study, we report the construction of an Infectivity-Selective Oncolytic Adenovirus (ISOAd), showing both selectivity for and potency against the target cancer cells. The ISOAd presented here has several important applications. For non-enveloped viruses, infection steps are mediated by protein binding, which is more specific than lipid membrane fusion. In this sense, transductional targeting of non-enveloped viruses such as, for example, adenovirus offers the possibility of designing targeted oncolytic vectors. This targeting of the oncolytic virus at the point of infection provides selectivity of the adenovirus vector on multiple levels: at the cellular level (e.g., selective replication), at the tissue level (e.g., cancer cell specific in situ distribution), and the organ level (e.g., reducing distribution to other organs). These three layers of selectivity can make the ISOAd more potent and more selective compared to current conditionally replicative adenoviruses, which solely depend on control during replication. In addition, the library screening technology established in this work may have broad applications for further development of targeted gene delivery approaches.

In the preceding description, particular embodiments may be described in isolation for clarity. Unless otherwise expressly specified that the features of a particular embodiment are incompatible with the features of another embodiment, certain embodiment can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Cell Lines

In this study, a human embryonic kidney cell line (HEK293 cells), pancreatic cancer cell lines (Panc1, AsPC-1, MiaPaCa2), and Chinese hamster ovarian cell lines (CHO) were used. All the cancer cell lines were obtained from AMERICAN TYPE CULTURE COLLECTION (ATCC; Rockville, MD). These cell lines were cultured in Dulbecco's modified Eagle's medium (DMEM) with 10% fetal bovine serum (FBS). 293-CRE cells, which express Cre recombinase stably, are derived from the HEK293 cell line (Palmer et al., 2003, Mol Ther 8:846-852). The 293-CRE-69 cells, which express 5/3-fiber and Cre recombinase, were generated by transfection of pDV69 into 293-CRE cells. The 644 cells express chimeric adenovirus fiber protein (adenovirus type 5 tail and shaft, and adenovirus type 3 knob). 644 cells and pDV69 were a general gift of Dr. GR Nemerrow, The Scripps Research Institute, La Jolla, CA (Von Seggern et al. 2000. J Virol. 74(1):354-362). 293-CRE cells were grown in DMEM with 10% FBS and 100 µg/ml hygromycin (Sigma-Aldrich, St. Louis, MO). 293-CRE-69 cells were grown in DMEM with 10% FBS, 100 µg/ml hygromycin and Zeocin 600µg/ml (Sigma-Aldrich, St. Louis, MO). 644 cells were grown in DMEM with 10% FBS and 600µg/ml Zeocin.

Shuttle Plasmids and Recombinant Adenovirus

The fiber-modified adenoviral shuttle plasmids include 76.1-100 map units (m.u.) of the adenoviral genome with a single loxP site at the E3 region deleted (79.4-84.8 m.u.) (FIG. 2(*a*)). The pBHI(Csp) plasmid has a Csp45I site in the HI-loop of the fiber knob and pBHIΔCAR(Csp) includes four point mutations in the AB-loop of the fiber knob that abolish CAR binding (Miura et al. 2007. Gene Ther. 14(20): 1448-1460. Epub 2007 Aug. 16). The pBHIΔCAR-fs(+) plasmid has the four AB-loop point mutations as well (Miura et al. 2007. Gene Ther. 14(20):1448-1460. Epub 2007 Aug. 16). The pBMLHI and pBHIΔCAR-fs(+) contain two incompatible Csp45I and SpeI restriction sites in the HI-loop to display random peptides. In both plasmids, one nucleotide was inserted between the Csp45I and SpeI recognition sites to shift the reading frame of the fiber knob (Miura et al. 2007. Gene Ther. 14(20):1448-1460. Epub 2007 Aug. 16). The pBHIΔCAR-GFP was constructed by inserting a cytomegalovirus immediate early enhancer/promoter (CMV promoter) and the green fluorescent protein (GFP) gene downstream of the loxP site of pBHIΔCAR(Csp) (Miura et al. 2007. Gene Ther. 14(20):1448-1460. Epub 2007 Aug. 16). The pMLABΔSK contains the deletion of a 1.8 kb NheI-MunI fragment from pBMLHI for the AB-loop mutants-library backbone plasmids.

The pML-VTIN and pML-THLS plasmids have a GTTACTATTAATCGGTCTGCG (SEQ ID NO:11) (VTINRSA, SEQ ID NO:12) sequence and ACTCATCTTTCTATTTATGCT (SEQ ID NO:13) (THLSIYA, SEQ ID NO:14) in the AB-loop of NheI-MunI fragment, respectively.

The adenoviral cosmid cAd-WT includes the 0-79.4 m.u. region of the adenovirus genome, which includes a wild-type E1 region and a single loxP site at 79.4 m.u. (Miura et al. 2007. Gene Ther. 14(20):1448-1460. Epub 2007 Aug. 16) (FIG. 2(a)). The cAd-WT was recombined with pBHIΔCAR (Csp), AdΔCAR-WT, or pML-VTIN to generate replication-competent adenovirus vectors with the VTINRSA (SEQ ID NO:12) sequence (AdMLWT-VTIN) and pML-THLS to generate replication-competent adenovirus vectors with the THLSIYA (SEQ ID NO:14) sequence (AdMLWT-THLS). The full-length recombinant adenovirus DNA was generated with the adenovirus cosmid and shuttle plasmid by Cre-mediated recombination in vitro. A shuttle plasmid was linearized by PacI and recombined with equal moles of an adenoviral cosmid by Cre recombinase in vitro to produce a full-length adenoviral DNA. For example, 5 μg of shuttle plasmid and 15 μg of adenoviral cosmid were mixed with 40 U of Cre (2 U per 1 mg of DNA) in 600 μl of reaction mixture at 37° C. for three hours. Then, to generate recombinant adenovirus vectors, 5 μg of recombinant adenoviral DNA was transfected by activated-dendrimer transfection reagent (Superfect Transfect Reagent; Qiagen, Valencia, CA) into 2×10$^6$ adenovirus-producing cells in 6-cm dish. (Miura et al. 2007. Gene Ther. 14(20):1448-1460. Epub 2007 Aug. 16).

Quantitative Analysis for Efficiency of Library Production

For quantification of viral copy number, crude viral lysates (CVLs) were eluted. 2% volumes of CVLs were treated with 1 U of DNaseI at 37° C. for 15 minutes. The DNA from DNaseI-treated CVL were purified with QIAamp Blood kit (Qiagen, Valencia, CA) following the manufacture's instruction. Quantification of viral DNA copy numbers was performed by real-time PCR as follows. The total viral copy number was determined with E4 primers by SYBRGreen and the recombinant viral copy number was determined with by TAQMAN Probe for GFP gene. Oligonucleotide sequence were GFP forward: 5'-TGACCCTGAAGTTCATCTGC-3' (SEQ ID NO:15); GFP reverse: 5'-GAAGTCGTGCTGCTTCATGT-3' (SEQ ID NO:16); GFP probe: 6FAM -ACCCTCGTGACCACCCTGAC-CTAC-TAMRA (SEQ ID NO:17); E4 forward: 5'-GGAGTGCGCCGAGACAAC-3' (SEQ ID NO:18); E4 reverse: 5'-ACTACGTCCGGCGTT CCAT-3' (SEQ ID NO:19).

With optimized concentrations of primers and probes, the components of real-time PCR mixture were designed to result in a master mix with a final volume of 25 μl. The control (no template) received 2.5 μl of water. Thermal cycling conditions were as follows: two minutes at 58° C., 10 minutes at 95° C., and 40 cycles of 15 seconds at 95° C. and one minutes at 60° C.

High Throughput Screening of a Fiber-modified Adenovirus Library Based on Replication Capability on the Target Cells The high throughput procedure of replication-based screening of adenovirus library was described in detail in. Miura et al., Gene Ther. 2007 October; 14(20):1448-60. Briefly, The 1×10$^7$ of Panc1 cells were seeded in 60-mm dishes. One day later, the cells were infected with an adenovirus library at a multiplicity of infection of 1, and two hours later the cells were washed with phosphate-buffered saline. After 5-7 days following the infection, the replicated adenoviruses were scratched from the cells. For each subsequent selection round on Panc1 cells, a 10% volume of the CVL from a preselected adenovirus library was reapplied to the target cells and the process was repeated 3-4 times.

PCR and Sequencing of Fiber-modified Adenovirus Library

PCR and sequencing of adenovirus library clones were performed on DNA extracted from the CVL of each selection, which served as a template for PCR using primers containing upstream and downstream sequences of the AB-loop: 5'-AAGCTAACTTTGTGGACCAC-3' (SEQ ID NO:20) and 5'-ACTGCCACATTTTGTTAAGA-3' (SEQ ID NO:21), and primers containing upstream and downstream sequences of the HI-loop: 5'-GAAACAGGAGACACAA CTTTCGAA-3' (SEQ ID NO:22) and 5'-ACTAGTC-CAAGTGCATACTCTATG-3' (SEQ ID NO:23). PCR products were cloned by TA cloning using TOPO® TA Cloning® Kits for Sequencing (Invitrogen, Carlsbad, Calif.). A single colony from the transformed bacteria was picked from an agar plate containing ampicillin and examined using colony-PCR with M13 forward primer 5'-GTAAAACGACGGC-CAG-3' (SEQ ID NO:24) and M13 reverse primer 5'-CA-GGAAACAGCTATGAC-3' (SEQ ID NO:25). The PCR products were purified with QIAquick PCR purification kit (Qiagen, Valencia, Calif.) following the manufacture's instruction and the sequencing were run with M13 forward primer.

Binding Assay

The cells were seeded in 6 cm dishes at 1×10$^7$ cells/dish. The next day, the cells were infected with viruses/virus pool at a multiplicity of infection of 100 vp/cell. The dishes were then incubated at 4° C. to allow viruses to bind to the cells while preventing them from entering into the cells. After incubation for two hours, the cells were harvested and washed with PBS two times. DNA was isolated from cells according to a standard protocol using QIAamp Blood mini kit. pPCR assay for E4 genes was performed with SYBR-Green.

Quantitative Analysis of Viral Replication

The cells were seeded in 6-cm dishes at 1×10$^7$ cells/dish. The next day, the cells were infected with viruses/virus pool at a multiplicity of infection of 0.1 vp/cell. After incubation at 37° C. for two hours, cells were washed with PBS and added to 2.5 ml of DMEM medium with 5% FBS. For replication analysis on Day 2 and Day 5, DNA from CVL of the infected cells were isolated using QIAamp Blood mini kit. pPCR assay for E4 genes was performed with SYBR-Green.

Example 2

Cells

A human embryonic kidney cell line (293 cells) and cancer cell lines (Panc-1, AsPC-1, MiaPaCa-2 and A549) were obtained from AMERICAN TYPE CULTURE COLLECTION (ATCC, Manassas, VA). 293CRE cell line, which stably expresses the CRE recombinase, was an isolated single clone from the 116 cell line (Palmer et al., 2003, Mol Ther 8: 846-852). The 293CRE-69 cells expressing both the Ad5/Ad3-fiber and the CRE recombinase were generated by transfecting 293CRE cells with the Ad5/Ad3-fiber expressing plasmid, pDV69. The 644 cells express the Ad5/Ad3 fiber. All cells were maintained in Dulbecco's modified Eagle medium (DMEM) with 4.5 g/L glucose, L-glutamine, and sodium pyruvate (Mediatech, Manassas, VA) with 10% fetal bovine serum (Hyclone Thermo Scientific, Logan, UT). All cells were cultured at 37° C. and 5% $CO_2$. The 293CRE cells were grown with 100 μg/ml of hygromycin (Invitrogen, Carlsbad, CA). 293CRE-69 cells were grown with hygromycin (100 µg/ml) and Zeocin (600 µg/ml, Invitrogen, Carlsbad, CA). 293-MSLN cells over-expressing mesothelin were established by transfection of mesothelin-expressing plasmid, pcDNA3.1-MSLN (mesothelin cDNA cloned into pcDNA3.1), and were grown with G418 (600µg/ml, Invitrogen, Carlsbad, CA).

Rescue Virus and Shuttle Plasmids

The rescue virus (AdMLΔF), generated with the shuttle plasmid pMLΔF, has a wild-type E1 gene, a single loxP site replacing the E3 gene, and a deletion of its fiber region (79.4-91.3 m.u.). This virus was produced and propagated in 644 cells for pseudotyping with the Ad5/Ad3-modified adenovirus fiber. pMLABΔSK, starting plasmids for AB-loop mutants, has the 1.8 kb NheI-MunI fragment of the fiber region (87.6-91.3 m.u.) deleted. The shuttle plasmids of the fiber library (pMLAB-lib) included a 76.1-100 map unit (m.u.) of the adenoviral genome with a single loxP site and library sequences in the AB-loop region of the fiber in place of the E3 region deleted (79.4-84.8 m.u.). The reporter shuttle, pBΔCAR-GFP, was constructed by inserting a CMV-promoter-driven green fluorescent protein (GFP) expression cassette at the downstream of a loxP site in the E3 region, and the AB-loop of the fiber-knob region possesses four point-mutations for ablating CAR-binding.

Shuttle Plasmid for AB-loop Library

The AB-loop random library was generated via three steps of PCR. The library sequence was generated as a synthetic oligonucleotide, 5'-AAGCTAACTTTGTGGACCACAC-CAGCTC CATCTCCTAAC(NNK)$_7$GATGCTAAACT-CACTTTGGTCTTAACAAAATGTGGCAGT-3' (N=A,T,G or C, K=G or T; SEQ ID NO:1). This fragment was amplified and ligated with the PCR-amplified adenovirus DNA fragments (upper-PCR: nt31508-32256, and lower-PCR: nt32324-32830). The resultant fragment was then amplified with the primers AB-upper-S (5'-AATTGCTAGC-CCTGCAAACATCAG-3'; SEQ ID NO:7) and AB-lower-AS (5'-AATTCAATTGAAAAATAAACACGTTGAA-3'; SEQ ID NO:10), and then cloned into pMLABΔSK.

Quantitative Analysis for the Adenoviral Copy Number Determination

Crude viral lysates (CVLs) were analyzed as described in Example 1.

Screening of a Fiber-modified Adenovirus Library

Ten dishes of 293-MSLN cells (1 10$^7$ cells/6cm dish) were infected with an Ad library at low multiplicity of infection (approximately 1 MOI) for two hours and then washed with PBS. After 5-7 days following the infection, the viral solution was rescued. For each subsequent round of screening, a ten to twenty percent of the viral solution volume from the previous round was re-infected to the target cells, and the screening processes were repeated 2-3 times. The DNA extracted from the viral solution of each round served as a template for a PCR amplification of the AB-loop region with the following primers; AB-loop-S 5'-AAGCTAACTTTGTGGACCAC-3' (SEQ ID NO:20) and AB-loop-AS 5'-ACTGCCACATTTTGTTAAGA-3' (SEQ ID NO:21). The PCR products were cloned with TOPO TA Cloning Kits for Sequencing (Invitrogen, Carlsbad, Calif.).

Binding and Replication Assay

One day after the cells were seeded (1 10$^7$ cells/6cm dish), the cells were infected with virus at 100 vp/cell. The dishes for binding assay were incubated at 4° C. for two hours to allow viruses to bind to cells while preventing internalization of the virus into the cells, and DNA was isolated after extensive wash with PBS. For analyzing virus replication, the dishes were incubated at 37° C. for 5 days. DNA isolation and qPCR for E4 genes were performed as described.

Binding Inhibition of Isolated Adenovirus with siRNA/Antibody

The 293-MSLN and Panc-1 cells were transfected with either a mesothelin siRNA oligonucleotide or a nonspecific scrambled siRNA at a final concentration of 100 nmol/L, using LIPOFECTAMINE2000 (Invitrogen, Carlsbad, CA). Mock transfection controls received only the transfection reagent. After 72 hours of siRNA transfection, the binding assay was performed. For antibody based inhibition, the 293-MSLN cells were treated with the monoclonal anti-mesothelin antibody at a final concentration of 5 µg/ml. After two hours of incubation at 4° C., the binding assay was performed.

Flow-cytometry

Cultured cells (210$^5$) were dissociated with Dissociation Buffer (Sigma-Aldrich, St Louis, Mo.). Primary antibody (100 µl, mouse anti-mesothelia monoclonal antibody (k1, Invitrogen, Carlsbad, Calif.) diluted 1:100) was added to the cells and incubated for 1 hour at 4° C. The cells were then washed, resuspended in 100 µl of a secondary antibody (FITC conjugated goat anti-mouse IgG diluted 1:100 for Panc1 cells, PE conjugated goat anti-mouse IgG (Jackson Immuno Research, West Grove, Pa.) diluted 1:100 for 293, 293-MSLN, A549, MiaPaCa-2, and AsPC-1 cells), and incubated for another half an hour at 4° C. Finally, cells were washed twice and analyzed on flow-cytometer (BD FACS Canto II: BD Biosciences, Franklin Lakes, N.J.).

In Vivo Experiment

To analyze the anti-tumor effect in an in vivo model, 2 10$^7$ of Panc-1 and MiaPaCa-2 cells were inoculated subcutaneously into the flank of the female nude mice, and 10$^{10}$ vp of the selected virus or control virus was intratumorally injected when the diameter reached 5-7 mm. The condition of the mice was monitored daily, and the tumor diameter was measured twice a week. The tumor volume was calculated as Width$^2$ Length/2. The animal experiments were performed in accordance with the institutionally-approved animal experimental protocol. In a separate experiment under same conditions, the mice were sacrificed at Day 5. The tumor specimens were cut in half; the first half was quickly frozen and kept at −80° C. until used, and the second half was fixed with buffered formaldehyde for immunostaining. The DNA was purified from frozen tumor tissue by using DNeasy Blood & Tissue Kit (Qiagen, Valencia, Calif.), and the adenoviral DNA copy number of the E4 region was quantified by qPCR starting from 20 ng DNA. The expression of adenoviral hexon protein in the tumor was analyzed by immunostaining. All slides were scanned at 100, 200, and 400 mag nification using aNikon Eclipse TS100 microscope.

In Vivo Distribution of the Systemically Injected Viruses.

The Panc-1 cell line (10$^6$ cells) were injected subcutaneously into athymic nude mice. When the tumors grew 5-7 mm in diameter, the mice were treated with 10$^{11}$ vp/10 µl PBS of either AdML-VTIN (with targeted fiber) or AdML-5WT (with wild type fiber) injected into the tail vein. After 48 hours, major organs and tumors were harvested. DNA was purified using DNEASY Blood & Tissue Kit (Qiagen, Valencia, CA), and the adenoviral DNA copy number of the E4 region was quantified by qPCR starting from 20 ng DNA. In addition, tumor DNA was analyzed at Day 7 after virus injection.

Statistical Analysis.

Statistical comparisons between two groups were evaluated by Student's t-test. Continuous variables were compared by Mann-Whitney-U test. All P-values were 2-sided, and a value of P<0.05 was considered to indicate statistically significant.

The complete disclosure of all patents, patent applications, and publications, and electronically available material (including, for instance, nucleotide sequence submissions in, e.g., GENBANK and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

```
Sequence Listing Free Text
                                              SEQ ID NO: 1
5'-AACGGTACACAGGAAACAGGAGACACAACTTTCGAA(NNK)₇ACTAG TCCAAGTGCATACTCTATGTCATTTTCATGG-3'
(N = A, T, G or C; K = G or T)

SEQ ID NO: 2
5'-GAAAC AGGAGACACAACTTTCGAA-3'

SEQ ID NO: 3
5'- CATAGAGTATGCACTTGGACT AGT -3'

SEQ ID NO: 4
5'-AAGCTAACTTTGTGGACCACACCAGCTCCATCTCCTAAC(NNK)₇GA

TGCTAAACTCACTTTGGTCTTAACAAAATGTGGCAGT-3'
(N = A, T, G or C; K = G or T)

SEQ ID NO: 5
5'-AAGCTAACTTT GTGGACCAC-3'

SEQ ID NO: 6
5'-ACTGCCACATTTTGTTAAGA-3'

SEQ ID NO: 7
5'-AATTGCTAGCCCTGCAAACATCAG-3' (AB-upper S)

SEQ ID NO: 8
5'-GGTCCACAAAGTTAGCTTATC-3'

SEQ ID NO: 9
5'-TTAACAAAATGT GGCAGTCAA-3'

SEQ ID NO: 10
5'-AATTCAATTGAAAAATAAACACGTTGAA-3' (AB-lower AS)

SEQ ID NO: 11
GTTACTATTAATCGGTCTGCG

SEQ ID NO: 12
VTINRSA

SEQ ID NO: 13
ACTCATCTTTCTATTTATGCT

SEQ ID NO: 14
THLSIYA

SEQ ID NO: 15
5'-TGACCCTGAAGTTCATCTGC-3'

SEQ ID NO: 16
5'-GAAGTCGTGCTGCTTCATGT-3'

SEQ ID NO: 17
6FAM-ACCCTCGTGACCACCCTGACCTAC-TAMRA

SEQ ID NO: 18
5'-GGAGTGCGCCGAGACAAC-3'

SEQ ID NO: 19
5'-ACTACGTCCGGCGTTCCAT-3'

SEQ ID NO: 20
5'-AAGCTAACTTTGTGGACCAC-3'

SEQ ID NO: 21
5'-ACTGCCACATTTTGTTAAGA-3'

SEQ ID NO: 22
5'-GAAACAGGAGACACAACTTTCGAA-3'

SEQ ID NO: 23
5'-ACTAGTCCAAGTGCATACTCTATG-3'

SEQ ID NO: 24
5'-GTAAAACGACGGCCAG-3'

SEQ ID NO: 25
5'-CAGGAAACAGCTATGAC-3'
```

What is claimed is:

1. A method comprising:
   infecting fiber transcomplementing mammalian host cells with an Ad5/3 pseudotyped, genetically fiberless rescue adenovirus, wherein the rescue adenovirus genome comprises a single loxP site, the host cells modified to express CRE recombinase;
   transfecting the host cells with a library of plasmids, each plasmid:
      comprising a loxP site; and
      encoding at least one detectable polypeptide comprising a fiber polypeptide comprising an AB-loop comprising a targeting ligand, wherein the library of plasmids comprises a plurality of detectable polypeptides;
   incubating the infected and transfected host cell under conditions effective to permit:
      recombination between the adenovirus genome and the plasmid, and
      production of recombinant adenovirus particles comprising at least one detectable polypeptide; and
   detecting the at least one detectable polypeptide.

2. The method of claim 1 wherein the loxP site is located in place of a deletion within E3 of the rescue adenovirus genome.

3. The method of claim 1 further comprising collecting crude viral lysate and re-infecting the host cell with adenovirus in the crude viral lysate.

4. The method of claim 3 further comprising one or more additional rounds of collecting crude viral lysate and re-infecting the host cell with adenovirus in the crude viral lysate.

5. The method of claim 1 completed in no more than about 48 hours after plasmid transfection.

6. The method of claim 1 wherein infecting the host cell comprises adding adenovirus to a culture of host cells at a multiplicity of infection of about 10,000 vp/cell.

7. The method of claim 1 wherein the fiber polypeptide comprises an AB-loop that comprises an amino acid sequence that specifically binds to mesothelin.

8. The method of claim 7 wherein the amino acid sequence comprises VTINRSA (SEQ ID NO:12).

9. The method of claim 1, wherein incubating the infected and transfected host cell produces an adenovirus library that has at least $10^{10}$ recombinant adenovirus particles comprising at least one detectable polypeptide.

* * * * *

UNITED STATES PATENT AND TRADEMARK OFFICE
CERTIFICATE OF CORRECTION

PATENT NO. : 10,208,304 B2
APPLICATION NO. : 13/447847
DATED : February 19, 2019
INVENTOR(S) : Masato Yamamoto and Yoshiaki Miura Page 1 of 1

It is certified that error appears in the above-identified patent and that said Letters Patent is hereby corrected as shown below:

In the Specification

Column 1, Line No. 12, after "CA094084" insert --, CA168448,--

Signed and Sealed this
Eighteenth Day of June, 2019

Andrei Iancu
*Director of the United States Patent and Trademark Office*